(12) United States Patent
Jenner et al.

(10) Patent No.: US 9,360,630 B2
(45) Date of Patent: Jun. 7, 2016

(54) OPTICAL-ELECTRICAL ROTARY JOINT AND METHODS OF USE

(75) Inventors: Robert K. Jenner, Lowell, MA (US); Duane De Jong, Elk Grove, CA (US); Jiyuan (John) Yin, Acton, MA (US)

(73) Assignee: Volcano Corporation, San Diego, CA (US)

( * ) Notice: Subject to any disclaimer, the term of this patent is extended or adjusted under 35 U.S.C. 154(b) by 416 days.

(21) Appl. No.: 13/695,704

(22) PCT Filed: Aug. 31, 2012

(86) PCT No.: PCT/US2012/053436
§ 371 (c)(1),
(2), (4) Date: May 16, 2013

(87) PCT Pub. No.: WO2013/033592
PCT Pub. Date: Mar. 7, 2013

(65) Prior Publication Data
US 2013/0223798 A1    Aug. 29, 2013

Related U.S. Application Data

(60) Provisional application No. 61/529,746, filed on Aug. 31, 2011.

(51) Int. Cl.
*G02B 6/36* (2006.01)
*G02B 6/32* (2006.01)

(52) U.S. Cl.
CPC ............... *G02B 6/3604* (2013.01); *G02B 6/32* (2013.01)

(58) Field of Classification Search
None
See application file for complete search history.

(56) References Cited

U.S. PATENT DOCUMENTS

| 3,301,258 A | 1/1967 | Werner |
| 3,617,880 A | 11/1971 | Cormack et al. |
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |

(Continued)

FOREIGN PATENT DOCUMENTS

| EP | 1041373 A2 | 10/2000 |
| EP | 01172637 A1 | 1/2002 |

(Continued)

OTHER PUBLICATIONS

Marks et al., 1992, By-Passing Immunization:Building High Affinity Human Antibodies by Chain Shuffling, BioTechnol., 10:779-783.

(Continued)

*Primary Examiner* — Uyen Chau N Lee
*Assistant Examiner* — Chad Smith
(74) *Attorney, Agent, or Firm* — Thomas C. Meyers; Brown Rudnick LLP

(57) ABSTRACT

The present invention relates generally to rotatable optical couplings, and more particularly to a manually separable and re-connectable optical-electrical rotary joint. The invention provides a manually separable optical-electrical rotary joint in which an optical signal and electrical signal are transmitted while a downstream component rotates relative to an upstream component, for example, as driven by a motor at the upstream component. Further, the downstream component can be easily manually unplugged from the upstream component.

1 Claim, 15 Drawing Sheets

(56) References Cited

U.S. PATENT DOCUMENTS

| | | |
|---|---|---|
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,593,973 A * | 6/1986 | Yoshida ............ A61B 1/00165 264/1.29 |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,140,289 A * | 8/1992 | Andrieu ................. H01P 1/067 333/256 |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |

(56) References Cited

U.S. PATENT DOCUMENTS

| | | |
|---|---|---|
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |

(56) References Cited

U.S. PATENT DOCUMENTS

| | | |
|---|---|---|
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |

(56) References Cited

U.S. PATENT DOCUMENTS

| | | |
|---|---|---|
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronnekleiv et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |

(56) References Cited

U.S. PATENT DOCUMENTS

| | | |
|---|---|---|
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1 | 11/2005 | Kimmel et al. |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childlers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1 | 7/2007 | Unal et al. |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0097223 A1* | 4/2008 | Strickler ............... A61B 5/6852 600/478 |
| 2008/0101667 A1 | 5/2008 | Begelman et al. |
| 2008/0108867 A1 | 5/2008 | Zhou |

(56) References Cited

U.S. PATENT DOCUMENTS

| | | |
|---|---|---|
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177138 A1 | 7/2008 | Courtney et al. |
| 2008/0177183 A1 | 7/2008 | Courtney et al. |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1* | 10/2009 | Courtney et al. ............ 600/463 |
| 2009/0269014 A1 | 10/2009 | Winberg et al. |
| 2009/0270695 A1 | 10/2009 | Mceowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1* | 12/2009 | Muller et al. ................ 600/466 |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1 | 4/2011 | Moore et al. |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0238061 A1 | 9/2011 | van Der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg |
| 2012/0004529 A1 | 1/2012 | Tolkowsky et al. |
| 2012/0004668 A1 | 1/2012 | Wallace et al. |
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |

(56) References Cited

U.S. PATENT DOCUMENTS

| | | |
|---|---|---|
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2178442 A1 | 4/2010 |
| EP | 2438877 A2 | 4/2012 |
| GB | 2280261 A | 1/1995 |
| JP | 2000-037355 A | 2/2000 |
| JP | 2000-262461 A | 9/2000 |
| JP | 2000-292260 A | 10/2000 |
| JP | 2000-329534 A | 11/2000 |
| JP | 2001-125009 A | 5/2001 |
| JP | 2001-272331 A | 10/2001 |
| JP | 2002-503134 A | 1/2002 |
| JP | 2002-088660 A | 3/2002 |
| JP | 2002-523162 A | 7/2002 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2004-004080 A | 1/2004 |
| JP | 2004-510132 A | 4/2004 |
| JP | 2004-528111 A | 9/2004 |
| JP | 2005-274380 A | 10/2005 |
| JP | 2005-533610 A | 11/2005 |
| JP | 2006-184284 A | 7/2006 |
| JP | 2006-266797 A | 10/2006 |
| JP | 2006-313158 A | 11/2006 |
| JP | 2007-510143 A | 4/2007 |
| JP | 2009-233001 A | 10/2009 |
| JP | 2009-536425 A | 10/2009 |
| JP | 2010-516302 A | 5/2010 |
| JP | 2010-516304 A | 5/2010 |
| JP | 2011-056786 A | 3/2011 |
| JP | 2011-508677 A | 3/2011 |
| JP | 2013-546256 A | 12/2013 |
| JP | 2014-501163 A | 1/2014 |
| JP | 2014-506806 A | 3/2014 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/44296 A1 | 8/2000 |
| WO | 01/11409 A2 | 2/2001 |
| WO | 03/032936 A1 | 4/2003 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/016434 A1 | 2/2006 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |
| WO | 2007/060973 A1 | 5/2007 |
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |

(56) References Cited

FOREIGN PATENT DOCUMENTS

| | | |
|---|---|---|
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-553.
Nissen, 2001, Coronary Angiography and Intravascular Ultrasound, American Journal of Cardiology, 87(suppl):15A-20A.
Nitenberg et al., 1995, Coronary vascular reserve in humans: a critical review of methods of evaluation and of interpretation of the results, Eur Heart J. 16(Suppl 1):7-21.
Oesterle et al., 1986, Angioplasty at coronary bifurcations: single-guide, two-wire technique, Cathet Cardiovasc Diagn., 12:57-63.
Oldenburg et al., 2003, Fast-Fourier-Domain Delay Line for In Vivo Optical Coherence Tomography with a Polygonal Scanner, Applied Optics, 42(22):4606-4611.
Pain et al., 1981, Preparation of protein A-peroxidase mono conjugate using a heterobifunctional reagent, and its use in enzyme immunoassays, J Immunol Methods, 40:219-20.
Persson et al., 1985, Acoustic impedance matching of medical ultrasound transducers, Ultrasonics, 23(2):83-89.
Kersey et al., 1991, Polarization insensitive fiber optic Michelson interferometer, Electron. Lett. 27:518-519.
Mindlin et al., 1936, A force at a point of a semi-infinite solid, Physics, 7:195-202.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Tanimoto et al., 2008, A novel approach for quantitative analysis of intracoronary optical coherence tomography: high inter-observer agreement with computer-assisted contour detection, Cathet Cardiovascular Intervent, 72(2):228-235.
Munson et al., 1980, Ligand: a versatile computerized approach for characterization of ligand-binding systems, Analytical Biochemistry, 107:220-239.
Smith et al., 1989, Absolute displacement measurements using modulation of the spectrum of white light in a Michelson interferometer, Applied Optics, 28(16):3339-3342.
Milstein et al., 1983, Hybrid hybridomas and their use in immunohistochemistry, Nature 305:537-539.
Soller, 2003, Polarization diverse optical frequency domain interferometry:All coupler implementation, Bragg Grating, Photosensitivity, and Poling in Glass Waveguides Conference MB4:30-32.
Stenqvist et al., 1983, Stiffness of central venous catheters, Acta Anaesthesiol Scand., 2:153-157.
Sutcliffe et al., 1986, Dynamics of UV laser ablation of organic polymer surfaces, Journal of Applied Physics, 60(9):3315-3322.
Vakhtin et al., 2003, Common-path interferometer for frequency-domain optical coherence tomography, Applied Optics, 42(34):6953-6958.
Verhoeyen et al., 1988, Reshaping human antibodies: grafting an antilysozyme activity, Science, 239:1534-1536.
Wang et al., 2009, Robust Guidewire Tracking in Fluoroscopy, IEEE Conference on Computer Vision and Pattern Recognition—CVPR 2009:691-698.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Felzenszwalb et al., 2005, Pictorial Structures for Object Recognition, International Journal of Computer Vision, 61(1):55-79.
Juviler et al., 2008, Anorectal sepsis and fistula-in-ano, Surgical Technology International, 17:139-149.
Kirkman, 1991, Technique for flow reduction in dialysis access fistulas, Surg Gyn Obstet, 172(3):231-3.
Wyawahare et al., 2009, Image registration techniques: an overview, International Journal of Signal Processing, Image Processing and Pattern Recognition, 2(3):11-28.
Suzuki, 2013, A novel guidewire approach for handling acute-angle bifurcations, J Inv Cardiol 25(1):48-54.
West et al., 1991, Arterial insufficiency in hemodialysis access procedures: correction by banding technique, Transpl Proc 23(2):1838-40.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filed May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
International Search Report and Written Opinion mailed on Jul. 30, 2014, for International Patent Application No. PCT/US14/21659, filed Mar. 7, 2014 (15 pages).
International Search Report and Written Opinion in PCT/US2012/053436 with international filing date Aug. 31, 2012, mailed Dec. 10, 2012 (9 pages).
International Search Report and Written Opinion in PCT/US2012/053270 with international filing date Aug. 31, 2012, mailed Nov. 20, 2012 (11 pages).
Amini et al., 1990, Using dynamic programming for solving variational problems in vision, IEEE Transactions on Pattern Analysis and Machine Intelligence, 12(9):855-867.
Abdi et al., 2010, Principal component analysis, Wiley Interdisciplinary Reviews: Computational Statistics 2:433-459.
Agresti, 1996, Models for Matched Pairs, Chapter 8, An Introduction to Categorical Data Analysis, Wiley-Interscience A John Wiley & Sons, Inc., Publication, Hoboken, New Jersey.
Akasheh et al., 2004, Development of piezoelectric micromachined ultrasonic transducers, Sensors and Actuators A Physical, 111:275-287.
Bain, 2011, Privacy protection and face recognition, Chapter 3, Handbook of Face Recognition, Stan et al., Springer-Verlag.
Breiman, 2001, Random forests, Machine Learning 45:5-32.
Burr et al., 2005, Searching for the Center of an Ellipse in Proceedings of the 17th Canadian Conference on Computational Geometry:260-263.
Fookes et al., 2002, Rigid and non-rigid image registration and its association with mutual information:A review, Technical Report ISBN:1 86435 569 7, RCCVA, QUT.
Cavalli et al., 2010, Nanosponge formulations as oxygen delivery systems, International Journal of Pharmaceutics 402:254-257.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.

(56) References Cited

OTHER PUBLICATIONS

Cook, 2007, Use and misuse of receiver operating characteristic curve in risk prediction, Circulation 115(7):928-93535.
D'Agostino et al., 2001, Validation of the Framingham coronary heart disease prediction score: results of a multiple ethnic group investigation, JAMA 286:180-187.
Davies et al., 1985, Plaque fissuring—the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Ergun et al., 2003, Capacitive Micromachined Ultrasonic Transducers:Theory and Technology, Journal of Aerospace Engineering, 16(2):76-84.
Fleming et al., 2010, Real-time monitoring of cardiac radio-frequency ablation lesion formation using an optical coherence tomography forward-imaging catheter, Journal of Biomedical Optics 15 (3):030516-030513.
Evans et al., 2006, Optical coherence tomography to identify intramucosa carcinoma and high-grade dysplasia in Barrett's esophagus, Clin Gast Hepat 4(1):38-43.
Grund et al., 2010, Analysis of biomarker data:logs, odds, ratios and ROC curves, Curr Opin HIV AIDS 5(6):473-479.
Gotzinger et al., 2005, High speed spectral domain polarization sensitive optical coherence tomography of the human retina, Optics Express 13(25):10217-10229.
Griffiths et al., 1994, Isolation of high affinity human antibodies directly from large synthetic repertoires, The EMBO Journal, 13(14):3245-3260.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
Bonnema, 2008, Imaging Tissue Engineered Blood Vessel Mimics with Optical Tomography, College of Optical Sciences dissertation, University of Arizona (252 pages).
International Search Report and Written Opinion mailed Nov. 2, 2012, for International Patent Application No. PCT/US12/53168, filed Aug. 30, 2013 (8 pages).
International Search Report and Written Opinion mailed Mar. 11, 2014, for International Patent Application No. PCT/US13/75675, filed Dec. 17, 2013 (7 pages).
International Search Report and Written Opinion mailed Mar. 19, 2014, for International Patent Application No. PCT/US13/075353, filed Dec. 16, 2013 (8 pages).
International Search Report and Written Opinion mailed on Apr. 14, 2014, for International Patent Application No. PCT/US2013/076148, filed Dec. 18, 2013 (8 pages).
International Search Report and Written Opinion mailed on Apr. 21, 2014, for International Patent Application No. PCT/US2013/076015, filed Dec. 18, 2013 (7 pages).
International Search Report and Written Opinion mailed on Apr. 23, 2014, for International Patent Application No. PCT/US2013/075328, filed Dec. 16, 2013 (8 pages).
International Search Report and Written Opinion mailed on Apr. 29, 2014, for International Patent Application No. PCT/US13/76093, filed Dec. 18, 2013 (6 pages).
International Search Report and Written Opinion mailed on Apr. 9, 2014, for International Patent Application No. PCT/US13/75089, filed Dec. 13, 2013 (7 pages).
International Search Report and Written Opinion mailed on Feb. 21, 2014, for International Patent Application No. PCT/US13/76053, filed Dec. 18, 2013 (9 pages).
International Search Report and Written Opinion mailed on Feb. 21, 2014, for International Patent Application No. PCT/US2013/076965, filed Dec. 20, 2013 (6 pages).
International Search Report and Written Opinion mailed on Feb. 27, 2014, for International Patent Application No. PCT/US13/75416, filed Dec. 16, 2013 (7 pages).
International Search Report and Written Opinion mailed on Feb. 28, 2014, for International Patent Application No. PCT/US13/75653, filed Dec. 17, 2013 (7 pages).
International Search Report and Written Opinion mailed on Feb. 28, 2014, for International Patent Application No. PCT/US13/75990, filed Dec. 18, 2013 (7 pages).
International Search Report and Written Opinion mailed on Mar. 10, 2014, for International Patent Application No. PCT/US2013/076212, filed Dec. 18, 2013 (8 pages).
International Search Report and Written Opinion mailed on Mar. 11, 2014, for International Patent Application No. PCT/US13/76173, filed Dec. 16, 2013 (9 pages).
International Search Report and Written Opinion mailed on Mar. 11, 2014, for International Patent Application No. PCT/US13/76449, filed Dec. 19, 2013 (9 pages).
International Search Report and Written Opinion mailed on Mar. 18, 2014, for International Patent Application No. PCT/US2013/076502, filed Dec. 19, 2013 (7 pages).
International Search Report and Written Opinion mailed on Mar. 18, 2014, for International Patent Application No. PCT/US2013/076788, filed Dec. 20, 2013 (7 pages).
International Search Report and Written Opinion mailed on Mar. 19, 2014, for International Patent Application No. PCT/US13/75349, filed Dec. 16, 2013 (10 pages).
International Search Report and Written Opinion mailed on Mar. 19, 2014, for International Patent Application No. PCT/US2013/076587, filed Dec. 19, 2013 (10 pages).
International Search Report and Written Opinion mailed on Mar. 19, 2014, for International Patent Application No. PCT/US2013/076909, filed Dec. 20, 2013 (7 pages).
International Search Report and Written Opinion mailed on Mar. 7, 2014, for International Patent Application No. PCT/US2013/076304, filed Dec. 18, 2013 (9 pages).
International Search Report and Written Opinion mailed on Mar. 7, 2014, for International Patent Application No. PCT/US2013/076480, filed Dec. 19, 2013 (8 pages).
International Search Report and Written Opinion mailed on Mar. 7, 2014, for International Patent Application No. PCT/US2013/076512, filed Dec. 19, 2013 (8 pages).
International Search Report and Written Opinion mailed on Mar. 7, 2014, for International Patent Application No. PCT/US2013/076531, filed Dec. 19, 2013 (10 pages).
International Search Report and Written Opinion mailed on Jan. 16, 2009, for International Patent Application No. PCT/US08/78963 filed on Oct. 6, 2008 (7 Pages).
Wang et al., 2011, In vivo intracardiac optical coherence tomography imaging through percutaneous access: toward image-guided radiofrequency ablation, J. Biomed. Opt. 0001 16(11):110505-110505-3.
Canny, 1986, A computational approach to edge detection, IEEE Trans. Pattern Anal. Mach. Intell. 8:679-698.
Maintz et al., 1998, An Overview of Medical Image Registration Methods, Technical Report UU-CS, (22 pages).
Jakobovits et al., 1993, Analysis of homozygous mutant chimeric mice:deletion of the immunoglobulin heavy-chain joining region blocks B-cell development and antibody production, PNAS USA 90:2551-255.
Jang et al., 2002, Visualization of Coronary Atherosclerotic Plaques in Patients Using Optical Coherence Tomography: Comparison With Intravascular Ultrasound, Journal of the American College of Cardiology 39:604-609.

(56) References Cited

OTHER PUBLICATIONS

Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Karp et al., 2009, The benefit of time-of-flight in PET imaging, J Nucl Med 49:462-470.
Kelly et al. 2005, Detection of Vascular Adhesion Molecule-1 Expression Using a Novel Multimodal Nanoparticle, Circulation Research 96:327-336.
Kheir et al., 2012, Oxygen Gas-Filled Microparticles Provide Intravenous Oxygen Delivery, Science Translational Medicine 4(140):140ra88.
Khuri-Yakub et al., 2011, Capacitive micromachined ultrasonic transducers for medical imaging and therapy, J Micromech Microeng. 21(5):054004-054014.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Larin et al., 2002, Noninvasive Blood Glucose Monitoring with Optical Coherence Tomography: a pilot study in human subjects, Diabetes Care, 25(12):2263-7.
Brown, 1992, A survey of image registration techniques, ACM Computing Surveys 24(4):325-376.
Little et al., 1991, The underlying coronary lesion in myocardial infarction:implications for coronary angiography, Clinical Cardiology, 14(11):868-874.
Loo, 2004, Nanoshell Enabled Photonics-Based Imaging and Therapy of Cancer, Technology in Cancer Research & Treatment 3(1):33-40.
Turk et al., 1991, Eigenfaces for Recognition, Journal of Cognitive Neuroscience 3(1):71-86.
Choma et al., 2003, Sensitivity Advantage of Swept Source and Fourier Domain Optical Coherence Tomography, Optics Express 11(18):2183-2189.
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Goel et al., 2006, Minimally Invasive Limited Ligation Endoluminal-assisted Revision (MILLER) for treatment of dialysis access-associated steal syndrome, Kidney Int 70(4):765-70.
Miller et al., 2010, The MILLER banding procedure is an effective method for treating dialysis-associated steal syndrome, Kidney International 77:359-366.
Morrison et al., 1984, Chimeric human antibody molecules: mouse antigen-binding domains with human constant region domains, PNAS 81:6851-6855.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Nygren, 1982, Conjugation of horseradish peroxidase to Fab fragments with different homobifunctional and heterobifunctional cross-linking reagents. A comparative study, J. Histochem. and Cytochem. 30:407.
Tuzel et al., 2006, Region Covariance: A Fast Descriptor for Detection and Classification, European Conference on Computer Vision (ECCV).
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Bail et al., 1996, Optical coherence tomography with the "Spectral Radar"-Fast optical analysis in volume scatterers by short coherence interferometry, Optics Letters 21(14):1087-1089.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4):1547-1556.
Pepe et al., 2004, Limitations of the odds ratio in gauging the performance of a diagnostic, prognostic, or screening marker, American Journal of Epidemiology 159(9):882-890.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Robbin et al., 2002, Hemodialysis Arteriovenous Fistula Maturity: US Evaluation, Radiology 225:59-64.
Sarunic et al., 2005, Instantaneous Complex Conjugate Resolved Spectral Domain and Swept-Source OCT Using 3x3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
Siwy et al., 2003, Electro-responsive asymmetric nanopores in polyimide with stable ion-current signal, Applied Physics A: Materials Science & Processing 76:781-785.
Smith, 1997, The Scientist and Engineer's Guide to Digital Signal Processing, California Technical Publishing, San Diego, CA:432-436.
Nezam, 2008, High Speed Polygon-Scanner-Based Wavelength-Swept Laser Source in the Telescope-Less Configurations with Application in Optical Coherence Tomography, Optics Letters 33(15):1741-1743.
Song et al., 2012, Active tremor cancellation by a "Smart" handheld vitreoretinal microsurgical tool using swept source optical coherence tomography, Optics Express, 20(21):23414-23421.
Strobl et al., 2009, An Introduction to Recursive Partitioning:Rationale, Application and Characteristics of Classification and Regression Trees, Bagging and Random Forests, Psychol Methods., 14(4):323-348.
Strickland, 1970, Time-Domain Reflectometer Measurements, Tektronix, Beaverton, OR, (107 pages).
Tonino et al., 2009, Fractional flow reserve versus angiography for guiding percutaneous coronary intervention, The New England Journal of Medicine, 360:213-224.

(56) References Cited

OTHER PUBLICATIONS

Toregeani et al., 2008, Evaluation of hemodialysis arteriovenous fistula maturation by color-flow Doppler ultrasound, J Vasc. Bras. 7(3):203-213.

Traunecker et al., 1991, Bispecific single chain molecules (Janusins) target cytotoxic lymphocytes on HIV infected cells, EMBO J., 10:3655-3659.

Trolier-McKinstry et. al., 2004, Thin Film Piezoelectric for MEMS, Journal of Electroceramics 12:7-17.

Tuniz et al., 2010, Weaving the invisible thread: design of an optically invisible metamaterial fibre, Optics Express 18 (17):18095-18105.

Urban et al., 2010, Design of a Pressure Sensor Based on Optical Bragg Grating Lateral Deformation, Sensors (Basel), 10(12):11212-11225.

Vakoc et al., 2005, Phase-Resolved Optical Frequency Domain Imaging, Optics Express 13(14):5483-5493.

Wang et al., 2006, Multiple biomarkers for the prediction of first major cardiovascular events and death, The New England Journal of Medicine, 355(25):2631-2639.

Villard et al., 2002, Use of a blood substitute to determine instantaneous murine right ventricular thickening with optical coherence tomography, Circulation, 105:1843-1849.

Forstner & Moonen, 1999, A metric for covariance matrices, In Technical Report of the Dpt of Geodesy and Geoinformatics, Stuttgart University, 113-128.

Waterhouse et. al., 1993, Combinatorial infection and in vivo recombination: a strategy for making large phage antibody repertoires, Nucleic Acids Res., 21:2265-2266.

Yaqoob et al., 2006, Methods and application areas of endoscopic optical coherence tomography, J. Biomed. Opt., 11, 063001-1-063001-19.

Yasuno et al., 2004, Polarization-sensitive complex Fourier domain optical coherence tomography for Jones matrix imaging of biological samples, Applied Physics Letters 85(15):3023-3025.

Zhang et al., 2004, Full range polarization-sensitive Fourier domain optical coherence tomography, Optics Express, 12(24):6033-6039.

Fatemi et al., 1999, Vibro-acoustography: an imaging modality based on ultrasound-stimulated acoustic emission, PNAS U.S.A., 96(12):6603-6608.

Griffiths et al., 1993, Human anti-self antibodies with high specificity from phage display libraries, The EMBO Journal, 12:725-734.

Harrison et al., 2011, Guidewire Stiffness: What's in a name?, J Endovasc Ther, 18(6):797-801.

Rollins et al., 1998, In vivo video rate optical coherence tomography, Optics Express 3:219-229.

Zitova et al., 2003, Image registration methods: A survey. Image and Vision Computing, 21(11):977-1000.

Wegener, 2011, 3D Photonic Metamaterials and Invisibility Cloaks: The Method of Making, MEMS 2011, Cancun, Mexico, Jan. 23-27, 2011.

Jiang et al., 1992, Image registration of multimodality 3-D medical images by chamfer matching, Proc. SPIE 1660, Biomedical Image Processing and Three-Dimensional Microscopy, 356.

Bouma et al., 1999, Power-efficient nonreciprocal interferometer and linear-scanning fiber-optic catheter for optical coherence tomography, Optics Letters, 24(8):531-533.

Blanchet et al., 1993, Laser Ablation and the Production of Polymer Films, Science, 262(5134):719-721.

Li et al., 2000, Optical Coherence Tomography: Advanced Technology for the Endoscopic Imaging of Barrett's Esophagus, Endoscopy, 32(12):921-930.

Bruining et al., 2009, Intravascular Ultrasound Registration/Integration with Coronary Angiography, Cardiology Clinics, 27(3):531-540.

Clarke et al., 1995, Hypoxia and myocardial ischaemia during peripheral angioplasty, Clinical Radiology, 50(5):301-303.

David et al., 1974, Protein iodination with solid-state lactoperoxidase, Biochemistry 13:1014-1021.

Adler et al., 2007, Phase-Sensitive Optical Coherence Tomography at up to 370,000 Lines Per Second Using Buffered Fourier Domain Mode-Locked Lasers, Optics Letters, 32(6):626-628.

Elghanian et al., 1997, Selective colorimetric detection of polynucleotides based on the distance-dependent optical properties of gold nanoparticles, Science, 277(5329):1078-1080.

Gould et al., 1974, Physiologic basis for assessing critical coronary stenosis, American Journal of Cardiology, 33:87-94.

Tearney et al., 1997, In vivo Endoscopic Optical Biopsy with Optical Coherence Tomography, Science, 276:2037-2039.

Brummer, 1997, An euclidean distance measure between covariance matrices of speechcepstra for text-independent speaker recognition, in Proc. South African Symp. Communications and Signal Processing:167-172.

Jakobovits et al., 1993, Germ-line transmission and expression of a human-derived yeast artificial chromosome, Nature 362:255-258.

Johnson et al., 1993, Human antibody engineering: Current Opinion in Structural Biology, 3:564-571.

Jones et al., 1986, Replacing the complementarity-determining regions in a human antibody with those from a mouse, Nature, 321:522-525.

Barnea et al., 1972, A class of algorithms for fast digital image registration, IEEE Trans. Computers, 21(2):179-186.

Sihan et al., 2008, A novel approach to quantitative analysis of intraluminal optical coherence tomography imaging, Comput. Cardiol:1089-1092.

Karapatis et al., 1998, Direct rapid tooling:a review of current research, Rapid Prototyping Journal, 4(2):77-89.

Kozbor et al., 1984, A human hybrid myeloma for production of human monoclonal antibodies, J. Immunol., 133:3001-3005.

Larin et al., 2004, Measurement of Refractive Index Variation of Physiological Analytes using Differential Phase OCT, Proc of SPIE 5325:31-34.

Kruth et al., 2003, Lasers and materials in selective laser sintering, Assembly Automation, 23(4):357-371.

Kumagai et al., 1994, Ablation of polymer films by a femtosecond high-peak-power Ti:sapphire laser at 798 nm, Applied Physics Letters, 65(14):1850-1852.

Lefevre et al., 2001, Stenting of bifurcation lesions:a rational approach, J. Interv. Cardiol., 14(6):573-585.

Fischler et al., 1973, The representation and matching of pictorial structures, IEEE Transactions on Computer 22:67-92.

\* cited by examiner

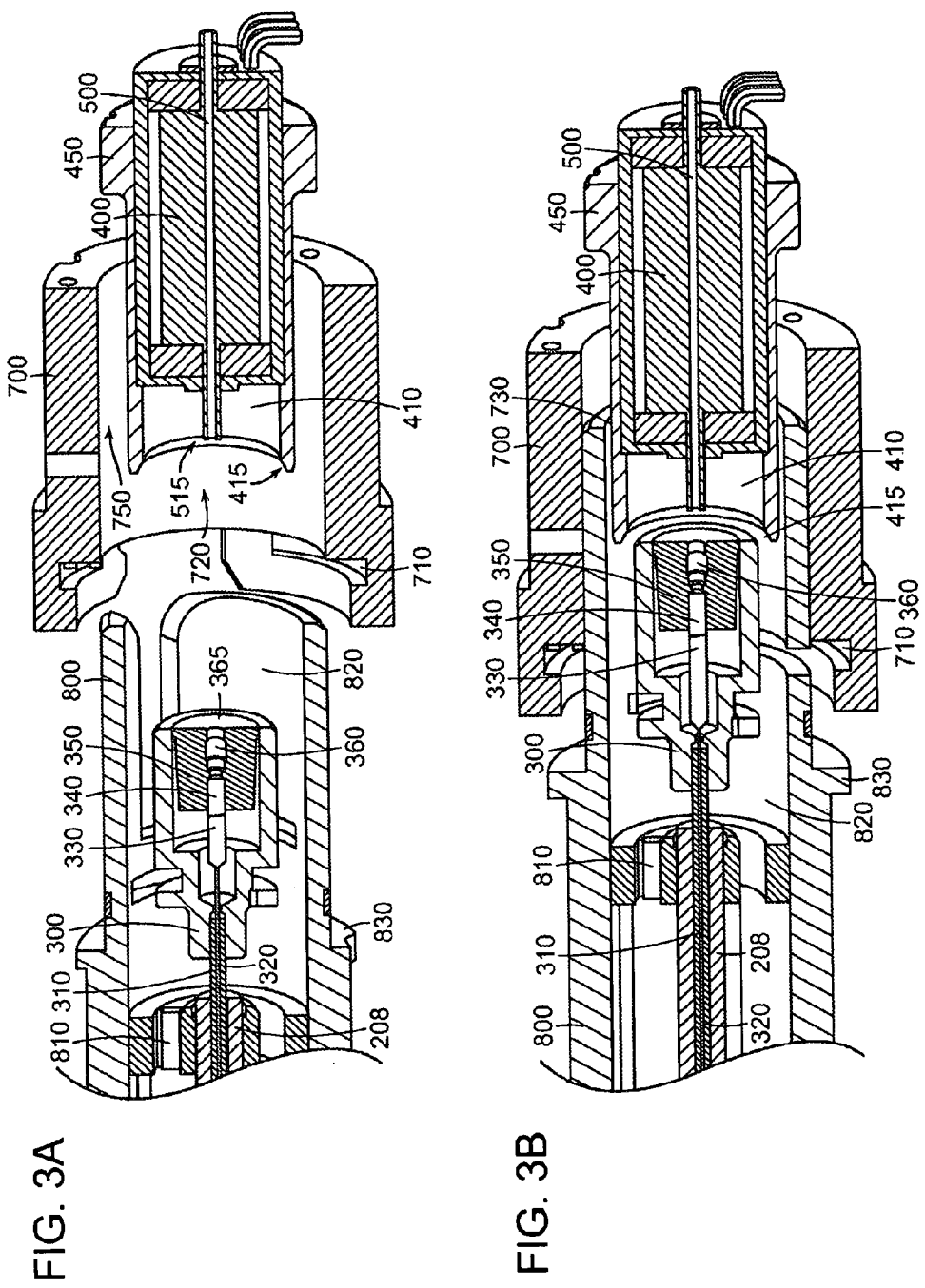

OPTICAL-ELECTRICAL ROTARY JOINT AND METHODS OF USE

CROSS-REFERENCE TO RELATED APPLICATION

This application claims priority to U.S. Provisional Application No. 61/529,746, filed Aug. 31, 2011, the contents of which are hereby incorporated by reference in their entirety.

FIELD OF THE INVENTION

The present invention relates generally to an optical rotary joint, and more particularly to a manually connectable and dis-connectable optical-electrical rotary joint.

BACKGROUND

Optical signals are used in such fields as communication, robotics, medical imaging, and navigational systems. For example, optical coherence tomography (OCT) involves imaging human tissue using optical fibers to carry the image signal. In OCT, an imaging engine uses a fiber optic catheter to send light into a patient's body to collect an image.

Electrical motors move the catheter into place and rotate it at speeds well above 10,000 RPM to collect the image. The rotation and the imaging are coordinated by a microchip in the imaging engine. The optical signal is digitized while electrical signals control the motors.

Where optical and electrical signals are transmitted together, joints present problems. For example, where a downstream component must rotate relative to an upstream instrument, a motor must be provided along the signal line to drive the rotation. Not only does arranging the signal lines around the motor pose logistical problems, the rotation causes problematic vibrations. For example, some optical couplings go out of alignment when rotated at 5,000 RPM.

Further, existing optical couplings are typically not easy to connect and dis-connect. To service or replace one component of an optical system can require replacement of the entire system or significant system down-time. Even a routine event such as sterilizing an imaging catheter can require a medical imaging system to be taken out of service because the catheter is fixed to the imaging engine.

SUMMARY

The invention provides a manually connectable optical-electrical rotary joint across which optical and electrical signals are transmitted while a motor drives rotation of a downstream component. The downstream component can be unplugged from an upstream instrument and easily swapped for another downstream component. Because the rotary joint allows the component to be uncoupled from the instrument, the component can be serviced or replaced while the instrument remains in operation. Further, the rotary joint is designed to operate at rotational speeds in excess of 10,000 RPM without going out of alignment. Since the optical-electrical rotary joint stays in alignment at high speeds and is manually swappable, the invention allows optical-electrical systems to be used more productively with minimal down-time and makes servicing or replacing individual components easier and less costly. For example, OCT systems can use disposable, interchangeable imaging catheters (e.g., sterile, single-use catheters). Thus, the imaging engine of an OCT system can stay in continuous operation while a separate catheter can be used for each image capture operation.

In certain aspects, the invention provides an optical-electrical rotary joint in which an optical line and an electrical conductor in an upstream instrument are coupled to a downstream component to provide optical and electrical transmission while allowing for rotation of the downstream component. The optical signal is transmitted across the junction even during rotation by an arrangement of lenses. Electrical signals can be conducted through one, or a plurality of, conductive lines. Constant electrical contact across a rotating joint may be provided by any suitable mechanism such as slip rings, torroidal springs, contact brushes, pogo pins, conductive bands, or combination thereof. A motor is provided to drive rotation of the downstream component. The motor can be fixed within the instrument, which can be, for example, a medical imaging system. In certain embodiments, the upstream member is provided by a patient interface module (PIM) of an OCT system.

In certain embodiments, the downstream component is provided as a plug, capable of being plugged into a corresponding jack on the upstream instrument. In this way, the upstream and downstream members may be manually separable and joinable. Because the elements can be easily separated and connected, one of the components may be easily removed for cleaning or can even be provided as a sterile, disposable components, such as a medical imaging device.

In related aspects, the invention provides methods for carrying current and light across a rotating joint, suitable for optical systems such as medical imaging systems. The methods includes transmitting light between an upstream instrument and a downstream component, conducting electricity from the instrument to the component, and rotating the component relative to the instrument while transmitting the light and conducting the electricity. Further, any number of distinct electrical signals can be simultaneously conducted (e.g., via different wires).

In some embodiments, methods include manually connecting the component to the instrument, separating them, or both. Rotation of the component can be driven by a motor at the instrument. In certain embodiments, the light is transmitted via an optical path that is coaxial with a drive shaft of the motor.

In some aspects, the invention provides a plug for a rotary joint housing a contact point coupled to an electrical conductor and an end of an optical line. The plug is adapted to be manually inserted into a corresponding jack in an instrument such that the plug member can rotate relative to a corresponding optical conductor and electrical line in the instrument. The optical line can be an optical fiber. A number of electrical contact points and conductors can be included. The plug member may have a male form factor such as, for example, a cylindrical sleeve disposed coaxially with the optical fiber. Use of the plug allows for manual connection and dis-connection of the electoral conductor and optical line to a corresponding line and conductor in in the jack. In certain embodiments, the plug is provided as an end of an optical imaging device such as an imaging catheter in an OCT system. In some aspects, the invention provides a jack for a rotary joint housing a contact point coupled to an electrical conductor and an end of an optical line.

In certain aspects, the invention provides an optical rotary joint. An optical rotary joint according to the invention accommodates an optical path between stationary and rotating optical components in which one component is disposed in the optical path outside one end of a drive shaft and the other component is disposed in the optical path outside the opposite end of the shaft. The optical components preferably are lenses; including concave, convex, double convex, planoconvex, double concave, plano-concave, and prisms. Commonly, one or both of the optical components are a collimator or collimating lens. For example, a stationary collimating lens is disposed in an optical path outside a proximal end of a drive shaft and a rotating collimating lens is disposed outside the distal end of the shaft in the same optical pathway. The optical components may be fixedly or removable attached to the drive shaft. The drive shaft is preferably hollow in order to accommodate the optical path.

In another embodiment, an optical rotary joint comprises an optical path between stationary and rotating components including a drive motor with a drive shaft adapted to accommodate the optical path. A stationary collimating lens is attached to the drive motor and disposed in the optical path outside a proximal end of the hollow drive shaft. A rotating collimating lens is attached to the hollow drive shaft and disposed in the optical path outside a distal end of the hollow drive shaft.

In a further embodiment, an optical rotary joint comprises an optical path between stationary and rotating components including a drive motor slidably held within a receiver and including a hollow drive shaft adapted to accommodate the optical path. A stationary collimating lens is removably attached to the drive motor and disposed in the optical path outside a proximal end of the hollow drive shaft. A rotating collimating lens is rotatably disposed within a first housing such that when the first housing is removably attached to the receiver, the rotating collimating lens is removably attached to the hollow drive shaft and disposed in the optical path outside a distal end of the hollow drive shaft.

The foregoing and other features and advantages are defined by the appended claims. The following detailed description of exemplary embodiments, read in conjunction with the accompanying drawings is merely illustrative rather than limiting, the scope being defined by the appended claims and equivalents thereof.

BRIEF DESCRIPTION OF THE DRAWINGS

In the accompanying figures, like elements are identified by like reference numerals among the several preferred embodiments of the present invention.

FIGS. 3A-3C illustrates the attachment of the components of an optical-electrical rotary joint housed within a catheter handle and a receiver.

DETAILED DESCRIPTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The invention provides an optical-electrical rotary joint A rotary joint of the invention is useful in a rotational optical system in which light and current each carry signals between stationary and rotating optical elements. A rotary joint of the invention comprises a connector that facilitates connection and disconnection of the stationary and rotating optical-electrical components. The rotary joint is useful in any optical system comprising stationary and rotating optical-electrical components. Such systems include an Optical Coherence Tomography ("OCT") system, or may comprise another type of imaging system, including by way of example and not limitation, Intravascular Ultrasound ("IVUS"), spectroscopy, RAMAN, alternative interferometric techniques, therapeutic or diagnostic delivery devices, pressure wires, etc. In the case of an optical imaging system, light sources can be any laser source, broadband source, super-luminescent diode, tunable source, and the like. Communication between proximal and distal ends of any rotational imaging system may be via any suitable medium such as, for example, wires, optics, including fiber optics, lens systems, wireless, RF, etc.

Figure 1:
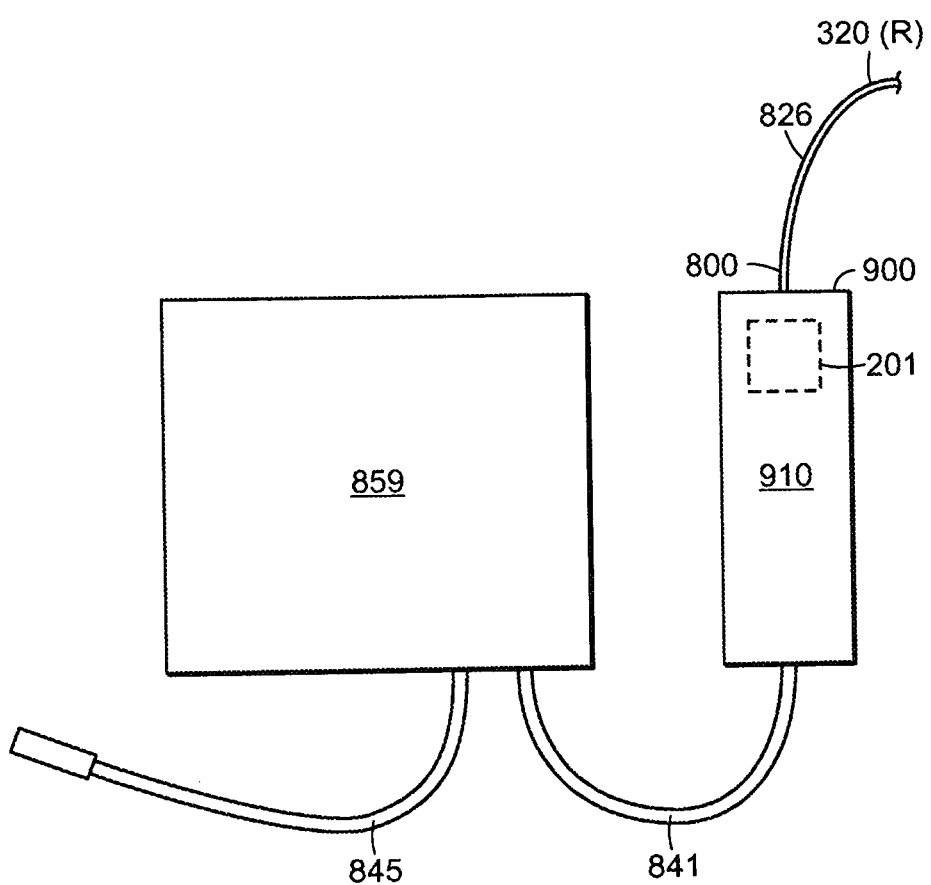
FIG. 1 shows components of an OCT system including a patient interface module (PIM).

FIG. 1 shows components of a system for OCT including a patient interface module (PIM) 900. An OCT system uses coherent light for imaging materials such as tissue of a patient. An OCT system may include an imaging engine 859 coupled to a workstation (e.g., a computer) via a connector 845. Imaging engine 859 is further connected to the patient interface module (PIM) 900 by connection line 841. The mechanics of PIM 900 can be housed in a durable housing 910.

An imaging catheter 826 extends from PIM 900 to an imaging target (e.g., patient). Inside imaging catheter 826 is disposed optical fiber 320. Imaging catheter 826 is connected to PIM 900 at a rotary joint 201 through catheter handle 800, described in more detail herein. As illustrated by FIG. 1, PIM 900 is stationary (S) relative to fiber 320, which rotates (R) (i.e., relative to PIM 900 and housing 910.

Figure 2:
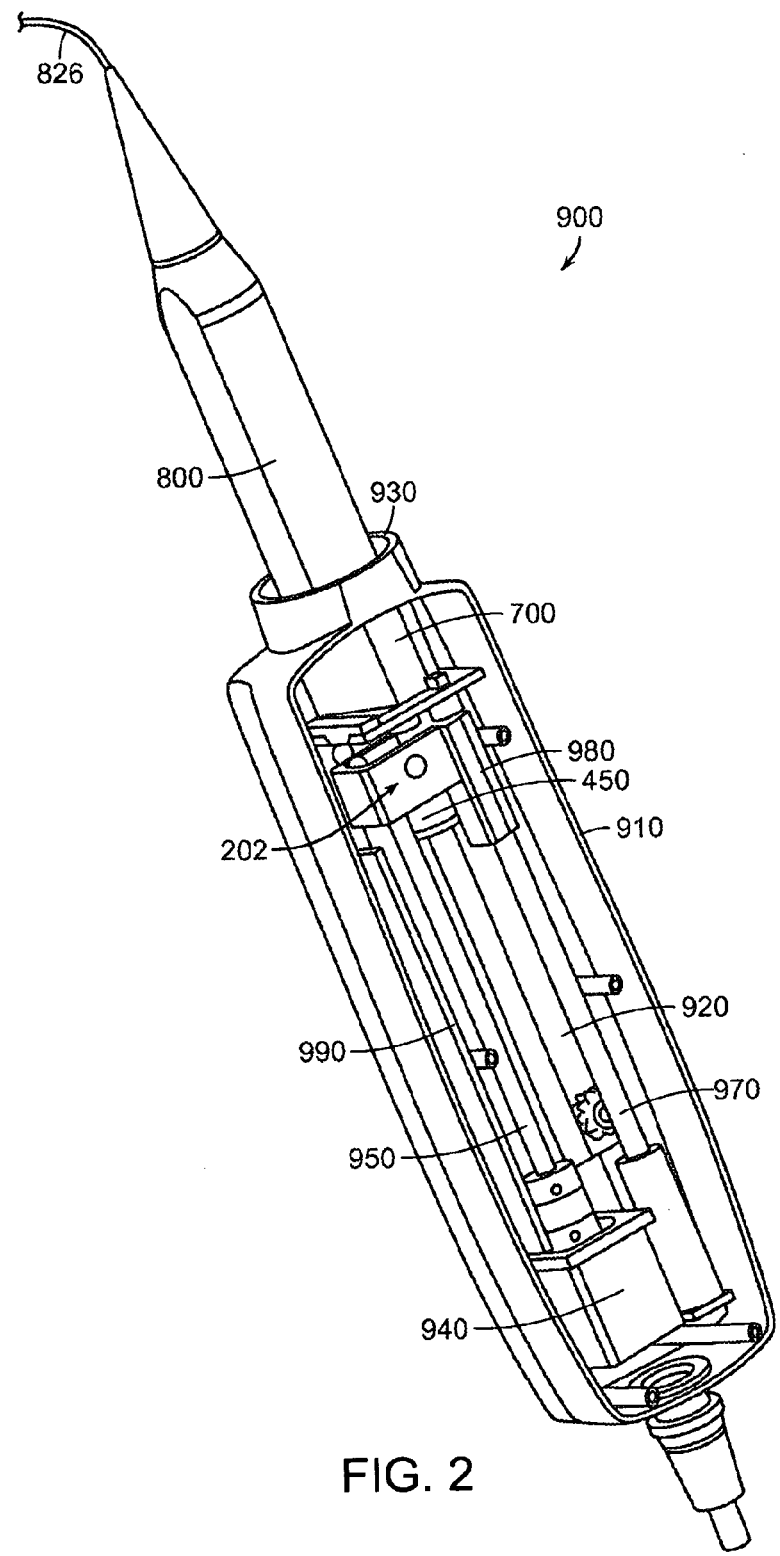
FIG. 2 illustrates a PIM accommodating an optical-electrical rotary joint.

FIG. 2 shows imaging catheter 826 connected to PIM 900 through the interaction of catheter handle 800 and receiver 700. As illustrated in FIG. 2, in some embodiments, PIM 900 includes a housing 910 accommodating a central seat 920 adapted to receive components of a rotary joint. For example, the PIM 900 includes a distal aperture 930 adapted to accommodate the receiver 700 removably attached to the catheter handle 800 as described herein with regard to FIGS. 3A-3C. The central seat 920 can also accommodate other components of an optical imaging system, for example a carriage or translatable drive stage 202 to accommodate the motor housing 450 (See FIGS. 3A-4C). The translatable drive stage 202 includes bearing 980 engaging guide rail 970 and lead screw 950 turned by motor 940 and controlled by circuit board 990.

In certain embodiments, motor housing 450 includes a motor to drive rotation of catheter 826. Motor 940 drives translation of drive stage 202, and thus translation of imaging catheter 826. By the combined rotation and translation of this apparatus, a distal end of the imaging catheter may take an image around and along the target tissue.

While imagining catheter 826 is being rotated by a motor mounted at motor housing 450, PIM housing 910 remains stationary (relative to the rotating imaging catheter). Due to the action of rotary joint 201, both optical communication and constant electrical contact are maintained across the junction between the rotating components and the stationary components.

In certain embodiments, rotary joint 201 is manually separable and re-connectable. A re-connectable optical electrical rotary joint can generally be described in terms of an upstream member or "jack" (e.g., housing 910 with receiver 700) and a downstream member or "plug" (e.g., catheter handle 800 including optical fiber 320).

Various mechanisms can provided constant electrical contact for one or more electrical lines across the joint. The electrical lines may include separate contact points for the rotary and connector functions. For example, in some embodiments, the rotary function is provided by a slip ring, and a separable, re-connectable connection is provided by conductive torroidal springs or pogo pins, discussed in greater detail below with reference to FIGS. 4A-7.

In certain embodiments, a single assembly provides rotary and connector functions. For example, a wire-brush slip ring assembly with clearance to support the axial connection motion can be included.

Figure 3C:
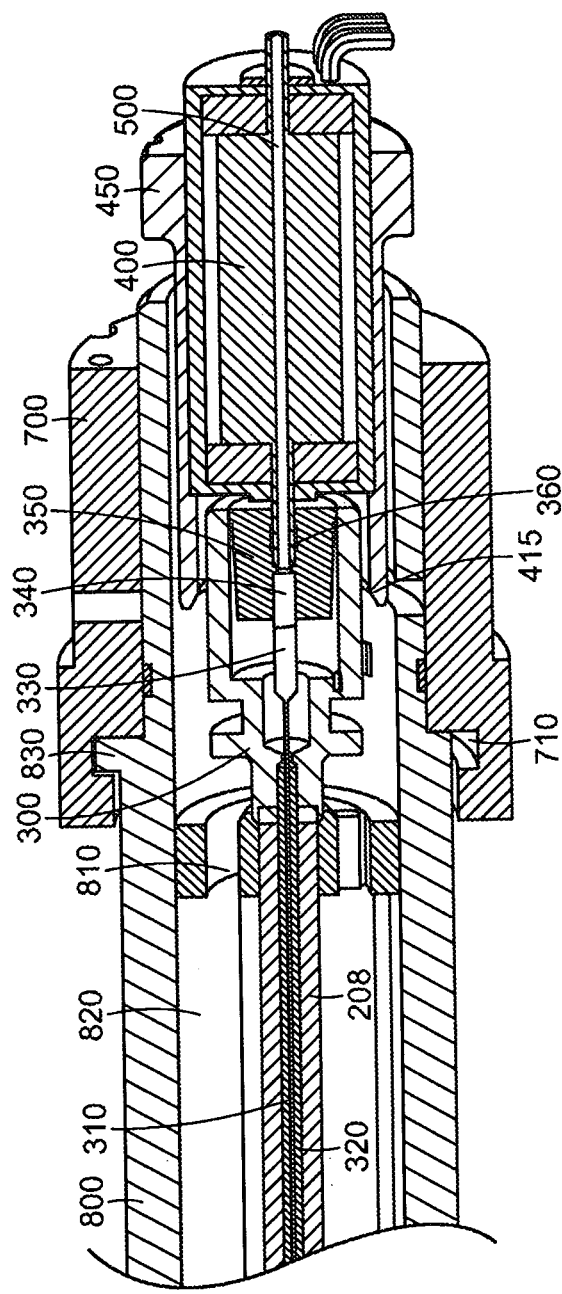

FIGS. 3A-3C illustrates catheter handle 800 coupling to receiver 700 to provide an operational rotary joint. For clarity, electrical lines and connections are not shown in FIGS. 3A-3C, and will be discussed with reference to FIGS. 4A-7 below. Catheter handle 800 may be provided as an end of imagining catheter 826 and receiver 700 may be mounted in PIM 900, as shown in FIG. 2.

As shown in FIGS. 3A-3C, a coupling 300 is provided at an end of imaging catheter 826 housed within catheter handle 800. Within receiver 700, motor housing 450 houses motor 400. Joining catheter handle 800 to receiver 700 (i.e., coupling imaging catheter 826 to PIM 900) positions coupling 300 within motor housing 450 so that rotary joint 201 transmits torque, translational forces, and optical and electrical signals.

To accomplish this, motor 400 is fixedly held within a lumen 410 longitudinally disposed through a motor housing 450 that may include or be attached to a carriage or longitudinally translatable drive stage 202 (see FIGS. 10A-10C) that provides longitudinal translation of the hollow drive shaft 500 (and the housing 450) relative to a receiver 700. The coupling 300 is coaxially disposed within catheter handle 800. A rigid shaft 310 rotates freely within a support housing 208 which is supported by a vibration dampening mechanism 810 that is fixedly disposed to an internal surface of catheter handle 800. Connections of the motor 400 to the motor housing 450 and the vibration dampening mechanism 810 to the internal surface may be by connection methods including by way of example and not limitation, a friction fit with or without shims, a weld, an adhesive, etc.

Referring to FIG. 3A, the receiver 700 includes a lumen 720 disposed longitudinally therethrough. The motor housing 450 is disposed coaxially within the lumen 720 such that an annular space 730 is defined between the exterior surface of the motor housing and the inner surface of the lumen 720. As illustrated in FIG. 3B, upon initial engagement of the catheter handle 800 and the receiver 700, the catheter handle 800 is accommodated by the annular space 730. Such accommodation creates a preliminary alignment of the coupling 300 with the lumen 410.

A tapered feature 415 may be disposed at a distal end of the lumen 410 and the motor housing 450. As illustrated in FIG. 3C, upon further coaxial engagement of the catheter handle 800 within the annular space 730 of the receiver 700, the coupling 300 is guided by the tapered feature 415 into coaxial accommodation with the lumen 410. In an alternative embodiment, a tapered guide feature may be implemented on the proximal end of the coupling 300 instead of, or in addition to, the tapered feature 415. Such accommodation creates in turn a preliminary coaxial alignment of a distal end hollow drive shaft 500 with the lumen 360.

Figure 4A:
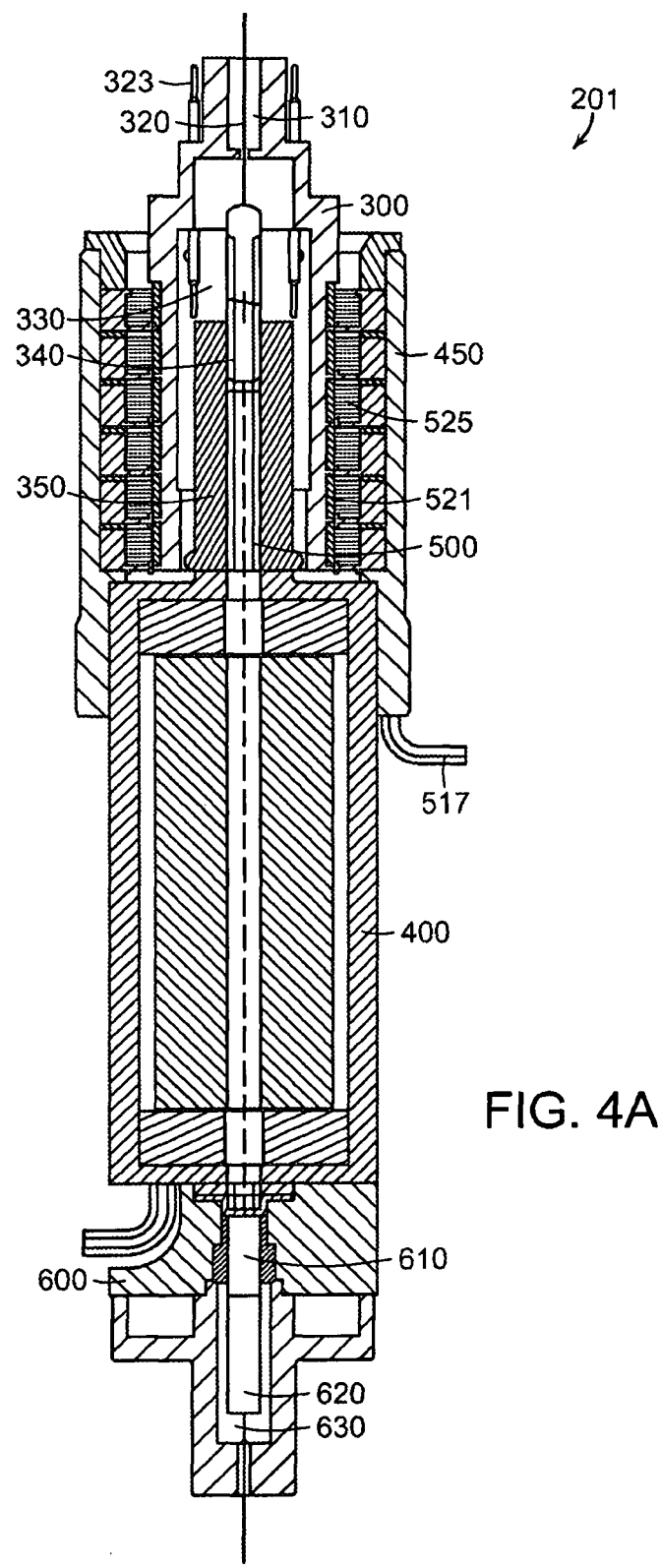
FIGS. 4A and 4B illustrate an optical-electrical rotary joint with slip rings and contact brushes according to certain embodiments.
Figure 4B:
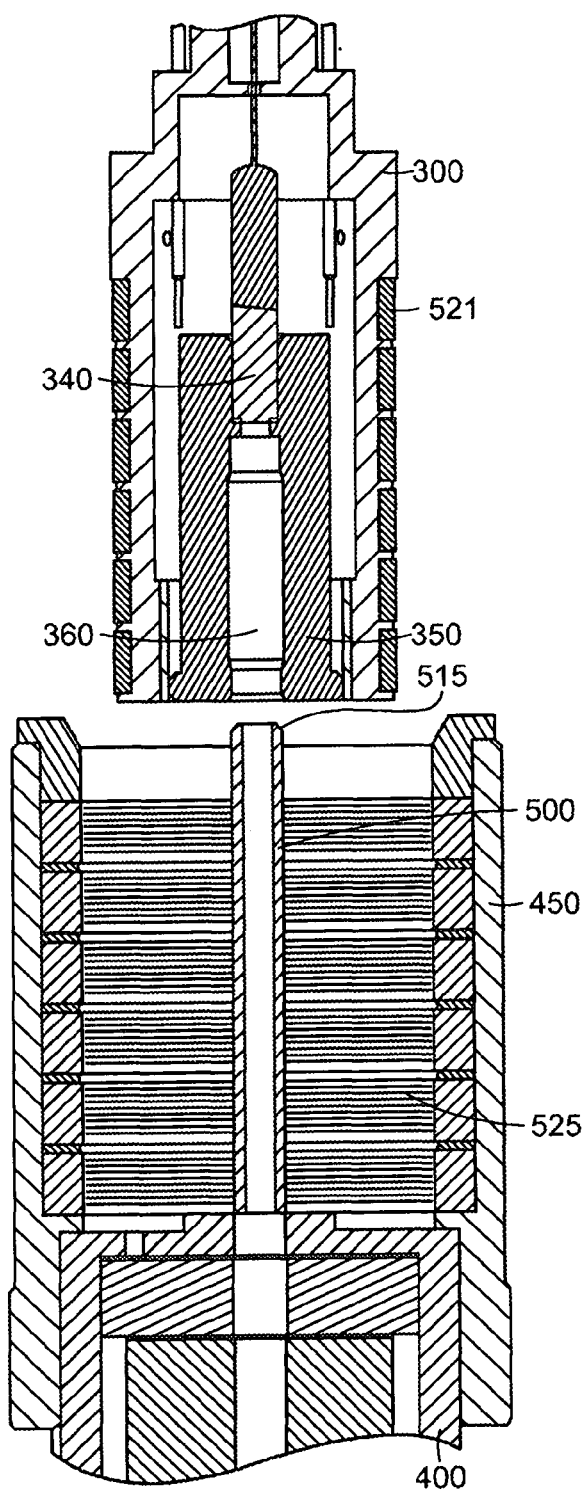

In certain embodiments, a distal end of the hollow drive shaft 500 includes an externally beveled feature 515 (see, e.g., FIG. 4B). In this embodiment, upon further engagement of the catheter handle 800 and the receiver 700, the lens holder 350 is guided by the beveled feature 515 to engage the lumen 360 and the hollow drive shaft 500. In some embodiments, a guide feature, for example, tapered feature 367 (see FIG. 9A) may be disposed at a proximal end of the lumen 360 instead of, or in addition to, beveled feature 515. The shape of the beveled features 415, 515, or the alternative embodiments may be straight or rounded to suit the intended use.

Figure 8A:
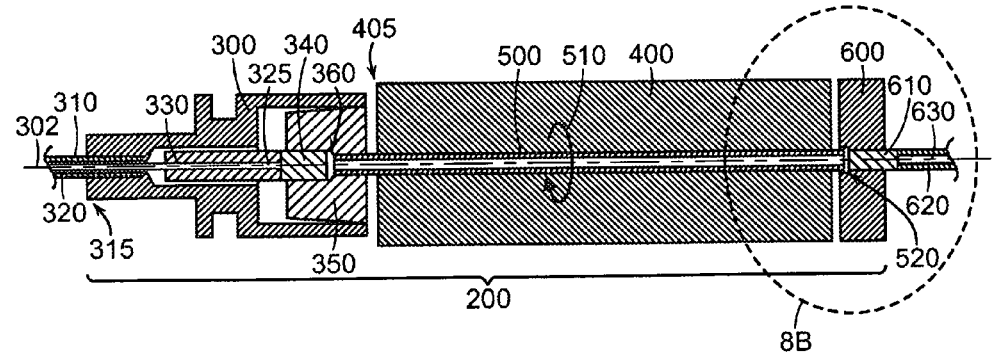
FIG. 8A illustrates a cross-sectional view of an embodiment of an optical rotary joint.

So aligned, the hollow drive shaft 500 may be removably attached within the lumen 360 (as described herein with regard to FIG. 8A). In an alternative embodiment, the engagement of the lumen 360 and the hollow drive shaft 500 may be effected by motion of the rotary drive motor 400 and associated components instead of, or in addition to, further engagement of the catheter handle 800 and the receiver 700.

Coincident with the removable attachment of the hollow drive shaft 500 within the lumen 360, the catheter handle 800 removably attaches to the receiver 700, by any method of removable attachment. For example, in one embodiment, slots 710 on the interior surface of the receiver 700 accommodate ribs 830 on the exterior surface of catheter handle 800. In this embodiment, as illustrated in FIGS. 3A-3C, the receiver 700 and the catheter handle 800 are oriented such that each rib 830 is disposed at an open end of each slot 710. So oriented, the receiver 700 is rotated relative to the catheter handle 800 so that each rib 830 enters each slot 710. Each rib 830 may further include a radial or longitudinal protrusion (not shown) at an end thereof that serves to snap onto a radial or longitudinal depression (not shown) within any or all of the slots 710. Such a snap fit may facilitate a locking attachment of the catheter handle 800 to the receiver 700, and the snap-locking bumps may be on the proximal face of the locking tab.

With handle 800 mounted in receiver 700 as shown in FIG. 3C, a functional optical-electrical rotary joint is provided, with coupling 300 at the downstream side of the joint and motor 400 at the upstream side of the joint. Further, the joint includes one or more of a contact point between a downstream electrical line and an upstream electrical line. Any suitable electrical contact point may be included. In some embodiments, an optical-electrical rotary joint is provided in which the electrical contact points employ one or more of a slip ring in contact with a contact brush; pogo pin; torroidal spring; ring contact; banded contact; cantilever; or combination thereof.

FIGS. 4A and 4B illustrate an optical-electrical rotary joint 201 with slip rings and contact brushes according to certain embodiments. As shown in FIG. 4A, in one embodiment, an exemplary optical rotary joint 201 comprises a coupling 300 operably coupled to a motor 400 having a hollow drive shaft 500, and a stationary lens holder 600 operably coupled to the proximal end of the hollow drive shaft 500. The hollow drive shaft 500 is rotationally driven by the motor 400. Referring to FIG. 4A, the coupling 300 is fixedly connected to a housing (e.g., rigid shaft 310) of a first optical fiber 320, which housing may also accommodate one or more electrical wires.

For electrical connection, joint 201 includes slip rings 521 in contact with contact brushes 525. As shown in FIG. 4B, slip rings 521 are mounted on an exterior surface of coupling 300 and are in electrically conductive contact-with first wires 323. Contact brushes 525 are disposed within motor housing 450 such that when the downstream plug member is inserted into the upstream jack member, each slip ring 521 makes electrical contact with a contact brush 525. Contact brushes 525 are each connected to one of second wires 517 so that when joint 201 is engaged, while stationary as well as while rotating, each of first wires 323 is in constant electrical contact with a corresponding one of second wires 517.

For optical connection, coupling 300 has mounted therein a shaft 310 configured for transmission of light. In one embodiment, shaft 310 is a hollow shaft that accommodates an optical fiber concentrically disposed therethrough. In another embodiment, shaft 310 may be a solid shaft or rod that is longitudinally transmissive to light similar to an optical fiber. Shaft 310 may be manufactured from a material, including by way of example and not limitation, stainless steel, titanium, beryllium, copper, alloys of titanium, beryllium and/or copper, ceramic material such as alumina, light transmissive material such as glass or plastic, and the like. The rigidity of a ceramic material may control vibration of the housing during rotational movement. Connection of the housing to the coupling 300 may be via a connection method including by way of example and not limitation, a frictional fit, a snap fit, crimping, swaging, over-molding, an adhesive, a weld, magnetic connection, and the like. Materials for the coupling 300 may be any metal or plastic, such as poly-ether-ether ketone (PEEK), and the like.

Referring to FIG. 4A, a first optical fiber 320 is disposed longitudinally through shaft 310 such that a first fiber ferrule 330 fixedly connects over an end of the first optical fiber 320. The first optical fiber 320 may be a single mode optical fiber, multi-mode optical fiber, and the like. The first fiber ferrule 330 can be made from a material that has properties similar to that of the first optical fiber 320. For example, the first fiber ferrule 330 may be made from glass to match coefficient of thermal expansion with the first optical fiber 320. The first optical fiber 320 may be connected to the first fiber ferrule 330 by a connection method including by way of example and not limitation, an adhesive, a weld, splicing, fusion, and the like. Alternatively, the first optical fiber 320 may be manufactured integrally with the first fiber ferrule 330.

The first optical fiber 320 is disposed approximately concentrically or coaxially within the shaft 310 and rotates with shaft 310. A distal end of shaft 310 may extend to a flexible drive cable of imaging catheter 826.

As shown in FIG. 4A, a first collimating lens 340 is disposed in optical communication with a proximal end of the first optical fiber 320, e.g., fixedly attached to the proximal end of the first fiber ferrule 330. The first collimating lens 340 may include an outer circumference or exterior surface that is coterminous with the exterior surface of the first fiber ferrule 330. The first collimating lens 340 may be attached to the first fiber ferrule 330 via a connection method including by way of example and not limitation, a frictional fit, a snap fit, a weld, an adhesive, and the like. The first fiber ferrule 330 facilitates stronger attachment of the first optical fiber 320 to the first collimating lens 340.

Figure 9A:
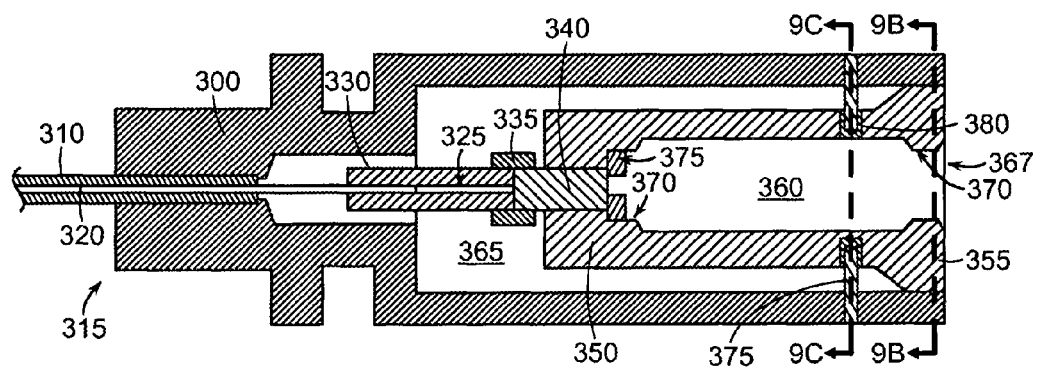
FIG. 9A is an enlarged cross-sectional view of the optical rotary joint of FIG. 8A.

In another embodiment, the first fiber ferrule 330 may be disposed within a ferrule sleeve or ring 335 to reinforce attachment of the first fiber ferrule 330 and the first collimating lens 340 (see, e.g., FIG. 9A and related discussion).

In certain embodiments, the first collimating lens 340 is fixedly held by a lens holder 350, for example, by a connection method including by way of example and not limitation, a frictional fit, a snap fit, an adhesive, a split sleeve with a clamping ring, and the like. The lens holder 350 may be manufactured from any material having suitable dimensional stability, suitable dynamic coefficient of friction, and suitable stiffness. Suitable materials for the lens holder 350 include by way of example and not limitation, stainless steel, aluminum, or thermoplastics such as polyetheretherketone (PEEK) or polyoxymethylene (POM), which is sold under the trademark DELRIN by E. I. du Pont de Nemours and Company, USA.

In another embodiment, the lens holder 350 may further be fixedly held to the proximal end of the first fiber ferrule 330. In another embodiment, the lens holder 350 may be further fixedly held to a proximal end of a ferrule sleeve. Connection of the lens holder 350 to fiber ferrule 330 (and/or to an optional ferrule sleeve) may be by a connection method including by way of example and not limitation, a frictional fit, a snap fit, a weld, an adhesive, and the like.

As shown in FIG. 4B, coupling 300 is manually separable from, and re-connectable to, motor housing 450. Accordingly, coupling 300 with catheter handle 800 together provide a "plug" that is separable from, and re-connectable to, a "jack" provided by receiver 700 and motor housing 450.

Referring to FIG. 4B, hollow drive shaft 500 extends from motor 400. A distal portion of the hollow drive shaft 500 is configured to be inserted into lens holder 350 and align with first collimating lens 340 when coupling 300 is coupled to housing 450 (i.e., when the plug is inserted into the jack). Insertion of coupling 300 into housing 450 may result in hollow drive shaft 500 being inserted into a lumen in lens holder 350. Preferably, hollow drive shaft 500 removably attaches within the lumen to facilitate removal and replacement of plug member 513 when in use in the field.

The lumen of lens holder 350 may include internal shoulders, which may facilitate precise alignment between hollow drive shaft 500 and lens holder 350 and/or removable attachment of the hollow drive shaft 500 within the lumen 360. The lumen of lens holder 350 may define a sloped interior portion dimensioned to accommodate the cross-sectional configuration of the drive shaft 500. As discussed below with reference to FIGS. 9A and 9C, lens holder 250 may include a stop for positioning collimating lens 340 and/or hollow drive shaft 500 within lens holder 350. The stop can hold lens 340, shaft 500, or both and prevent the relative motion of the parts.

The coupling 300 accommodates shaft 310, the first fiber ferrule 330, the first collimating lens 340, lens holder 350, and first wire(s) 323 in a way that transfers torque from the hollow drive shaft 500 to coupling 300, but also inhibits vibration of the apparatus from affecting angular alignment of the first collimating lens 340. This may be achieved by a configuration that provides for co-rotation or simultaneous rotation of the first optical fiber 320, the first fiber ferrule 330, collimating lens 340, and wire(s) 323 with the device without rigid or fixed attachment therebetween. The fit-up of drive shaft 500 and lens holder 350 is tightly controlled to provide more axial force and torque than is required to move the catheter core in its sheath and less axial force than would damage the bearings of motor 400. Shoulders within lens holder 350 help control the spring constant and hence grip on the shaft. Elasticity and coefficient of thermal expansion of the lens holder 350 material are both carefully chosen to provide the required range of engagement force and torque over the require range of operating conditions, especially at rotational speeds as high as between about 10,000 and 20,000 RPM.

Figure 9B:
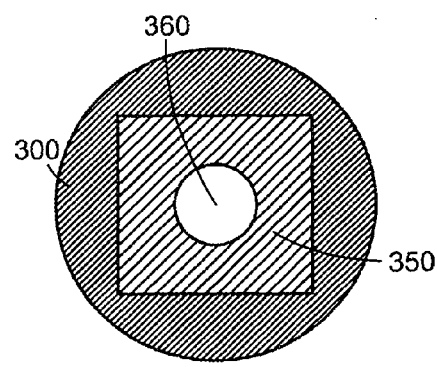
FIG. 9B is a cross-sectional view along the line 9B-9B of FIG. 9A.

In certain embodiments, lens holder 350 engages the coupling 300 by having a cross-sectional shape that is not free to rotate within coupling 300 (see, e.g., FIG. 9B). Lens holder 350 and coupling 300 may include any complementary shape that does not allow their relative rotation, such as polygonal, triangular, pentagonal, hexagonal, octagonal, trapezoidal, and the like. Thus, the lens holder 350 is not fixedly held to the coupling 300; however, rotation of the lens holder 350 is coupled to rotation of the coupling 300, which, in turn is coupled to rotation of the housing.

Vibration of shaft 310 may be reduced by decoupling transfer of moments between the lens holder 350 and the coupling 300 in a direction transverse to the longitudinal axis. Such decoupling may be achieved, for example, by a configuration including a plurality of pins presented by an inner surface of coupling 300 to a circumferential groove in an outer surface of the lens holder 350 (see FIGS. 2A and 2C). The pins may be spring loaded and biased inward, or may be press fit through holes in coupling 300. Such a pin-and-groove configuration facilitates longitudinal application of force between the lens holder 350 and the coupling 300 without a fixed or rigid connection therebetween.

The design reduces the effect of vibration of housing on the angular alignment of collimating lens 340.

In some embodiments, roll or rotation is transmitted by the square end of the lens holder 350 engaging the square pocket in the coupling 300. Pitch and yaw, which are the transverse angular alignments to the roll/rotation, are left free. Longitudinal force, "Z", is transmitted by the pins 375 in groove 380. Transverse forces, "X" and "Y", are transmitted by the square end/square pocket apposition. In one embodiment, at least 2 pins 375 transmit a longitudinal force while allowing the pitch and yaw motion, as described above. This may be precisely symmetric with respect to pitch and yaw motions or asymmetric with respect to the pitch and yaw motions. Alternatively, the pins 375 could also provide transverse restraint.

The hollow drive shaft 500 is rotationally driven by the motor 400. In one embodiment, the motor 400 is disposed concentrically around the hollow drive shaft 500. Such an arrangement may facilitate a reduction in the number of moving parts and a reduction in size of the optical rotary joint 201. In other embodiments, the motor 400 may include a separate housing 450 and be disposed apart from the hollow drive shaft 500 such that the hollow drive shaft 500 is driven by the motor 400 via, for example, an external gear train, belt, chain, or other mechanism for transfer of torque from the motor 400 to the hollow drive shaft 500 as may be known in the art. An exemplary motor 400 capable of producing rotational speeds in excess of 10,000 RPM, alternatively between about 10,000 and 20,000, is the Maxon DC motor sold by Maxon Precision Motors, Inc. (Fall River, Mass.).

As shown in FIG. 4A, hollow drive shaft 500 freely rotates proximate to a second collimating lens 610 fixedly held within stationary lens holder 600. The stationary lens holder 600 receives an end of hollow drive shaft 500. The second collimating lens 610 is optically coupled to the optical path within the hollow drive shaft 500. The stationary lens holder 600 may be attached to the motor 400 via a connection method including by way of example and not limitation, a frictional fit, a snap fit, crimping, swaging, overmolding, an adhesive, a weld, a magnetic fit, and the like. A second fiber ferrule 620 is attached to the second collimating lens 610. The second fiber ferrule 620 fixedly connects to a second optical fiber 630, as shown in FIG. 4A, which delivers light to and/or receives light from the second collimating lens 610 from a light source (not shown), such that the light may pass from the second optical fiber 630 to the collimating lens 610. In one embodiment, an end of the second optical fiber 630 is coaxially disposed with the second fiber ferrule 620. The second optical fiber 630 may be a single mode or multi-mode optical fiber. The second fiber ferrule 620 is made from a material that has properties similar to that of the second optical fiber 630. For example, the second fiber ferrule 620 may be made from glass to match coefficient of thermal expansion with the second optical fiber 630. The second optical fiber 630 may be connected to the second fiber ferrule 620 by a connection method including by way of example and not limitation, an adhesive, a weld, splicing, fusion, etc. Alternatively, the second optical fiber 630 may be manufactured integrally with the second fiber ferrule 620.

As shown in FIG. 4A, the second collimating lens 610 is disposed in optical communication with a distal end of the second optical fiber 630. The second collimating lens 610 may be made from an optical material having an internally variable index of refraction and may be the same as or different from the first collimating lens 340. For example, in one embodiment, the second collimating lens 610 is a lens having a radial index gradient such as a gradient index ("GRIN") or self focusing ("SELFOC") lens. In other embodiments, other types of collimating lenses may be used, such as devices that narrows a beam of light or causes the directions of motion to become more aligned in a specific direction (i.e. collimated or parallel) or to cause the spatial cross section of the beam to become smaller.

In one embodiment, the second collimating lens 610 is fixedly attached to the distal end of the second fiber ferrule 620. The second collimating lens 610 may be attached to the second fiber ferrule 620 via a connection method including by way of example and not limitation, a frictional fit, a snap fit, an adhesive, etc. It is contemplated that the second fiber ferrule 620 facilitates stronger attachment of the second optical fiber 630 to the second collimating lens 610.

In another embodiment, the second collimating lens 610 is fixedly held by the stationary lens holder 600 by a connection method including by way of example and not limitation, a frictional fit, a snap fit, an adhesive, etc. The stationary lens holder 600 may be manufactured from a material including by way of example and not limitation, stainless steel, aluminum, or plastics such as polyetheretherketone (PEEK) or polyoxymethylene (POM).

Electrical contact may be provided by any suitable mechanism. In certain embodiments, for example, as shown in FIGS. 4A and 4B, electrical contact is provided by slip rings and contact brushes. Other electrical contact mechanisms are provided including, for example, ring contacts, pogo pins, and cantilever contacts.

Figure 5A:
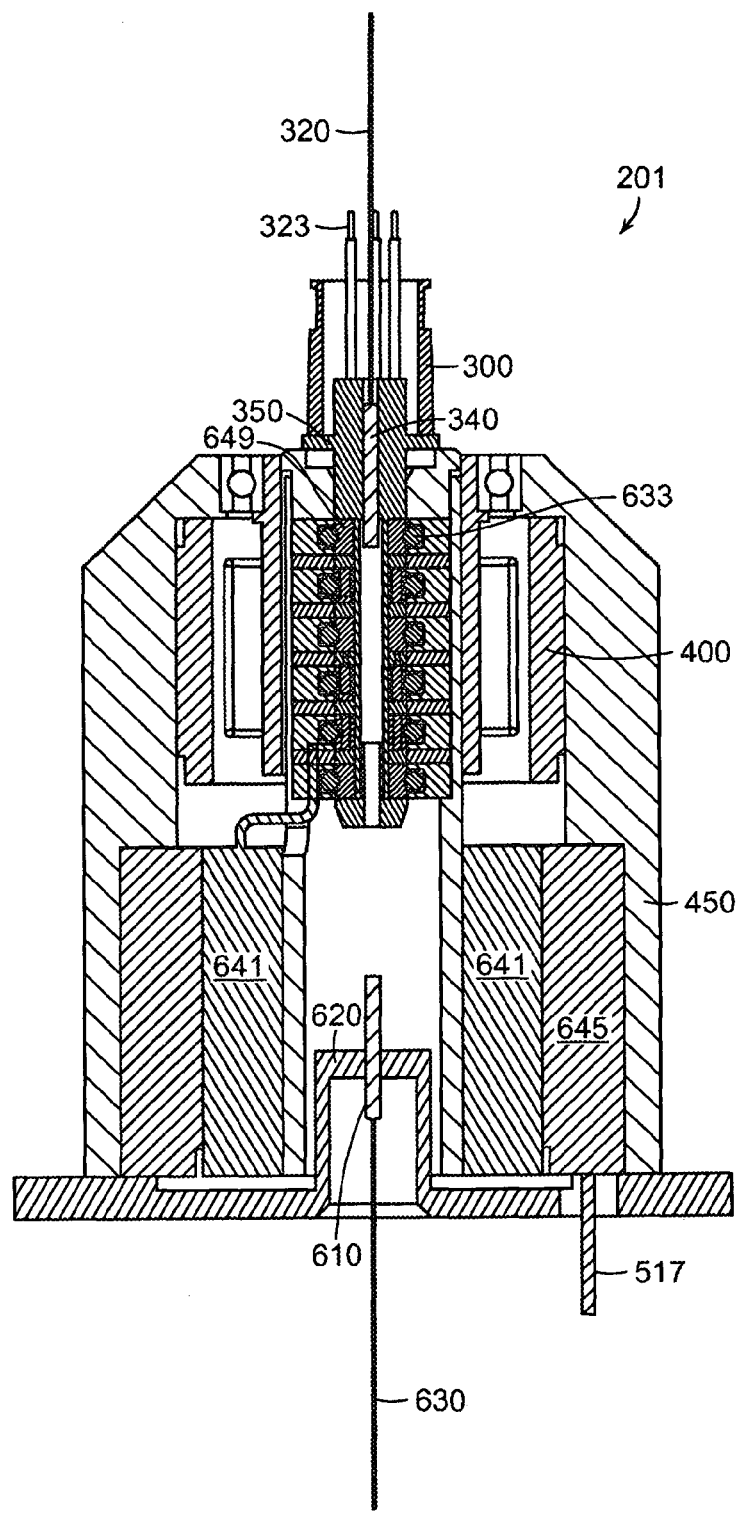
FIGS. 5A and 5B illustrate an optical electrical rotary joint with ring contacts according to certain embodiments.
Figure 5B:
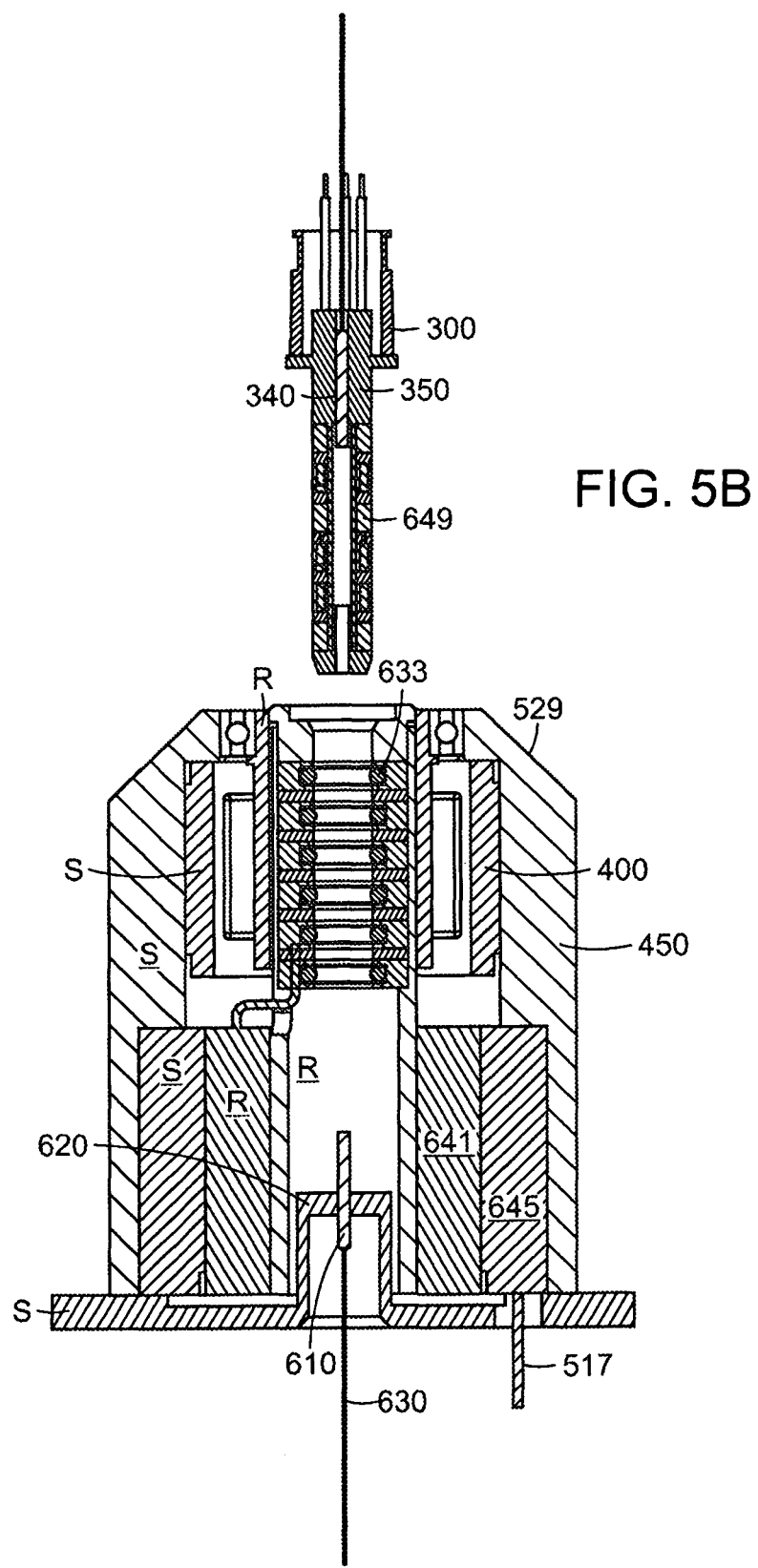

FIGS. 5A and 5B illustrate an optical electrical rotary joint with ring contacts according to certain embodiments. As shown in FIG. 5A, first wires 323 enter a distal end of coupling 300. Each of first wires 323 is in electrical contact with one of banded contacts 649 on an outer surface of lens holder 350. As shown in FIG. 5B, lens holder 350 and coupling 300 cooperate to define a plug member configured to be inserted into a lumen of jack member 529. Within jack member 529, a number of ringed contacts 633 are disposed to each make contact with one of banded contacts 649.

Jack member 529 is fixed to a set of rotating slip rings 641, which rotate relative a set of stationary permanent slip rings

645. As shown in FIG. 5B, R indicates a component that rotates relative to the components marked with an S. Jack member 529 is mounted within motor 400, which drives its rotation. Stationary slip rings 645 are mounted within motor housing 450 and each in contact with one of second wires 517.

As discussed above with reference to FIGS. 4A and 4B, optical communication across rotary joint 203 is provided by an optical path through first collimating lens 340 held by lens holder 350 and second collimating lens 610 mounted through a second fiber ferrule 620.

While rotating (R) components are rotating relative to stationary (S) components, optical communication and constant electrical contact are maintained across rotary joint 203 by the optical path and electrical contacts. Light is transmitted between first optical fiber 320 and second optical fiber 630 while current is transmitted along first wires 323 and second wires 517.

Figure 6:
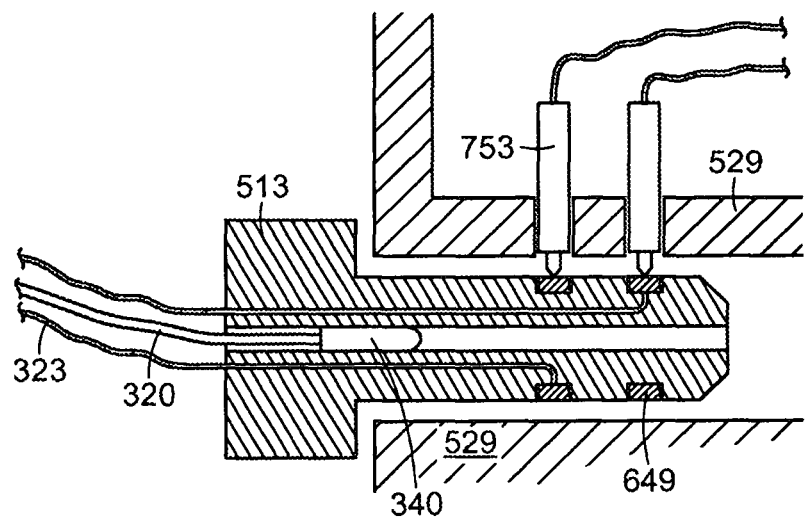
FIG. 6 shows an electrical connection made with pogo pins.

Other electrical contact mechanisms are included within the invention. For example, FIG. 6 shows an electrical connection made with pogo pins. For the sake of clarity, only certain components are shown in FIG. 6. First wires 323 enter coupling 300 and are connected to contact bands 649. Each of the contact bands 649 is in contact with at least one of pogo pins 753 mounted within jack member 529. In some embodiments (pictured), jack member 529 remains stationary relative to coupling 300. In certain embodiments, jack member 529 and coupling 300 are stationary relative to each other and rotate together relative to an upstream motor and associated hardware with electrical connection maintained through slip rings (as illustrated, for example, in FIG. 5A).

Figure 7:
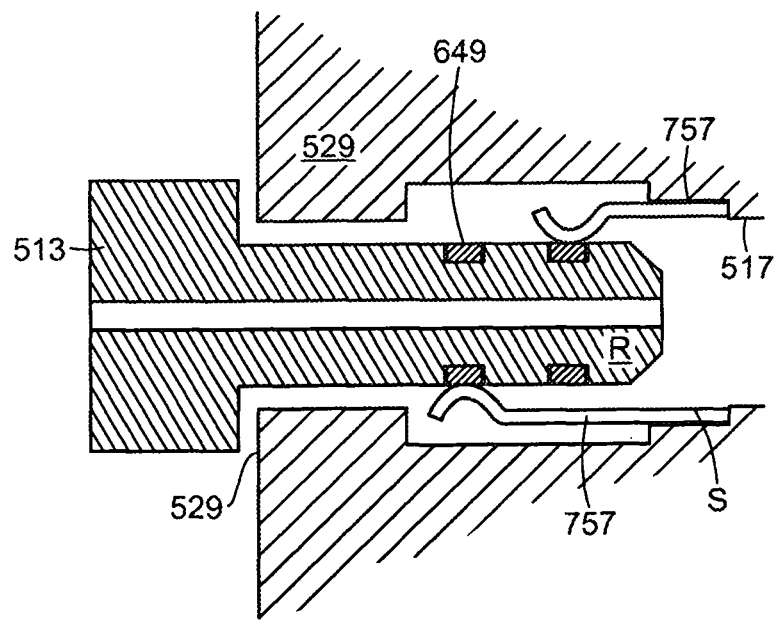
FIG. 7 shows an electrical connection provided by cantilevers.

In some embodiments, electrical contact is provided through the use of conductive cantilevered tabs in the form of one or more of cantilever 757, as shown in FIG. 7. As shown in FIG. 7, within coupling 300, wires can be connected to one or more band member 649. Each of band member 649 makes electrical contact with one of cantilever 757 provided with jack member 529. In some embodiments (pictured), jack member 529 remains stationary relative to coupling 300. In certain embodiments, jack member 529 and coupling 300 are stationary relative to each other and rotate together relative to an upstream motor and associated hardware with electrical connection maintained through slip rings (as illustrated, for example, in FIG. 10A).

As discussed above, the invention provides a manually separable and re-connectable optical-electrical rotary joint. Through the use of a joint of the invention, a component of an optical-electrical system such as an OCT system can be easily connected to, and separated from, another component. For example, an imaging catheter can be connected to a PIM in an OCT system. Because the optical-electrical rotary joint is easy and quick to connect and affordable to manufacture, an imaging catheter (or other component) can be provided that is disposable or designed for easy removal for sterilization.

Because the patient imaging component (the catheter) can be disconnected from the operating hardware (PIM 900 and imaging engine 859), the operating hardware can be kept in constant operation even when any given imaging component is taken out of service (e.g., for replacement or cleaning).

In some systems, rotational electrical contact is not needed. Accordingly, in some aspects and embodiments, the invention provides an optical rotary joint, such as a fiber-optic rotary joint (FORJ). In certain embodiments, an optical rotary joint such as a FORJ is manually separable and re-connectable.

Generally speaking, an optical rotary joint facilitates alignment and transmission of light between rotating optical components and stationary optical components. As shown in FIG. 8A, in one embodiment, an exemplary optical rotary joint 200 comprises a coupling 300 operably coupled to a motor 400 having a hollow drive shaft 500, and a stationary lens holder 600 operably coupled to the proximal end of the hollow drive shaft 500. The hollow drive shaft 500 is rotationally driven by the motor 400, as indicated by arrow 510. The longitudinal axis 302 of the first is generally shown in the x-axis direction, while the transverse axis is generally shown in the y-axis.

Referring to FIGS. 8A and 9A, the coupling 300 is fixedly connected to a rigid shaft 310 that extends from a distal end 315 of the coupling 300, such that the rigid shaft 310 rotates with the coupling 300. In one embodiment, the rigid shaft 310 is a hollow shaft that accommodates an optical fiber concentrically disposed therethrough. In another embodiment, the rigid shaft 310 may be a solid shaft or rod that is longitudinally transmissive to light similar to an optical fiber. The rigid shaft 310 may be manufactured from a material, including by way of example and not limitation, stainless steel, titanium, beryllium, copper, alloys of titanium, beryllium and/or copper, ceramic material such as alumina, light transmissive material such as glass or plastic, and the like. The rigidity of a ceramic material may control vibration of the rigid shaft 310 during rotational movement. Connection of the rigid shaft 310 to the coupling 300 may be via a connection method including by way of example and not limitation, a frictional fit, a snap fit, crimping, swaging, overmolding, an adhesive, a weld, magnetic connection, and the like. Materials for the coupling 300 may be any metal or plastic, such as polyetheretherketone (PEEK), and the like.

Referring to FIGS. 8A and 9A, a first optical fiber 320 is disposed longitudinally through the rigid shaft 310 such that a first fiber ferrule 330 fixedly connects over a proximal end 325 of the first optical fiber 320. The first optical fiber 320 may be a single mode optical fiber, multi-mode optical fiber, and the like. The first fiber ferrule 330 is made from a material that has properties similar to that of the first optical fiber 320. For example, the first fiber ferrule 330 may be made from glass to match coefficient of thermal expansion with the first optical fiber 320. The first optical fiber 320 may be connected to the first fiber ferrule 330 by a connection method including by way of example and not limitation, an adhesive, a weld, splicing, fusion, and the like. Alternatively, the first optical fiber 320 may be manufactured integrally with the first fiber ferrule 330.

The first optical fiber 320 is disposed approximately concentrically or coaxially within the rigid shaft 310 and rotates with the rigid shaft 310. The rigid shaft 310 connects on a distal end thereof to another portion of a flexible drive cable (not shown) ultimately including an optical probe (not shown) at a distal end of the flexible drive cable. Examples of a flexible drive cable, an imaging system including an optical probe rotating at a distal end of a flexible drive cable, may be found, for example, in Dick et al., U.S. Pub. 2009/0018393; Kemp et al., U.S. Pub. 2009/0046295; and Castella, et al., U.S. Pub. 2009/0043191, all of which are hereby incorporated by reference in their entirety herein.

As shown in FIG. 9A, a first collimating lens 340 is disposed in optical communication with a proximal end of the first optical fiber 320. The first collimating lens 340 may be made from an optical material having an internally variable index of refraction. For example, in one embodiment, the first collimating lens 340 is a lens having a radial index gradient. Such a lens, known in the art as a gradient index ("GRIN") or self-focusing ("SELFOC") lens facilitates the ability to precisely focus light using a simple, compact lens geometry, (NSG Europe, Belgium). In other embodiments, other types of collimating lenses as known in the art may be used.

In one embodiment, the first collimating lens 340 is fixedly attached to the proximal end of the first fiber ferrule 330. The first collimating lens 340 may include an outer circumference or exterior surface that is coterminous with the exterior surface of the first fiber ferrule 330. The first collimating lens 340 may attached to the first fiber ferrule 330 via a connection method including by way of example and not limitation, a frictional fit, a snap fit, a weld, an adhesive, and the like. The first fiber ferrule 330 facilitates stronger attachment of the first optical fiber 320 to the first collimating lens 340.

In another embodiment, referring to FIG. 9A, the first fiber ferrule 330 may be disposed within a ferrule sleeve or ring 335 to reinforce attachment of the first fiber ferrule 330 and the first collimating lens 340. The ferrule sleeve 335 may be circular or polygonal configuration that tightly fits over the exterior surface of the first fiber ferrule 330 and first collimating lens 340. The ferrule sleeve 335 may be manufactured from a material including by way of example and not limitation, metal, stainless steel, poly-methyl-methacrylate (PMMA), other plastic, and the like. The ferrule sleeve 335 may attach over the first fiber ferrule 330 and/or the first collimating lens 340 via a press fit, an adhesive, a snap fit, magnetic fit, or other methods of attachment.

In one embodiment, the first collimating lens 340 is fixedly held by a lens holder 350. In this embodiment, for example referring to FIGS. 8A and 9A, the first collimating lens 340 is disposed within or engaged with a distal end of a lumen 360 disposed longitudinally through the proximal end of the lens holder 350 by a connection method including by way of example and not limitation, a frictional fit, a snap fit, an adhesive, a split sleeve with a clamping ring, and the like. The lens holder 350 may be manufactured from any material having suitable dimensional stability, suitable dynamic coefficient of friction, and suitable stiffness. Suitable materials for the lens holder 350 include by way of example and not limitation, stainless steel, aluminum, or thermoplastics such as polyetheretherketone (PEEK) or polyoxymethylene (POM), which is sold under the trademark DELRIN by E. I. du Pont de Nemours and Company, USA.

In another embodiment, the lens holder 350 may further be fixedly held to the proximal end of the first fiber ferrule 330. In another embodiment, the lens holder 350 may be further fixedly held to a proximal end of the ferrule sleeve 335. In yet a further embodiment, the lens holder 350 may further be fixedly held to the proximal ends of both the first fiber ferrule 330 and the ferrule sleeve 335. Connection of the lens holder 350 to either or both of the fiber ferrule 330 and the ferrule sleeve 335 may be by a connection method including by way of example and not limitation, a frictional fit, a snap fit, a weld, an adhesive, and the like.

Referring to FIG. 8A, a distal portion of the hollow drive shaft 500 longitudinally extends from a distal end 405 of the motor 400. The distal portion of the hollow drive shaft 500 attaches within the lumen 360 that includes an opening on a proximal side of the lens holder 350 such that the hollow drive shaft 500 is longitudinally and coaxially aligned with the first collimating lens 340. Attachment of the hollow drive shaft 500 within the lumen 360 of the lens holder 350 may be by a connection method including by way of example and not limitation, a frictional fit, a snap fit, an adhesive, a weld, and the like. In one embodiment, the hollow drive shaft 500 removably attaches within the lumen 360 to facilitate removal and replacement of the motor 400 when in use in the field.

Referring to FIG. 9A, the lumen 360 is illustrated as having a luminal surface including one or more internal shoulders 370 at the proximal and distal ends of the lumen 360, which may facilitate precise alignment between hollow drive shaft 500 and lens holder 350 and/or removable attachment of the hollow drive shaft 500 within the lumen 360. In one embodiment, the internal shoulders 370 is a sloped inner diameter (ID) of the lumen 360, whereby the distal end of the motor shaft 500 abuts with the internal shoulders 370. In one embodiment, the ID is cylindrical or polygonal as to accommodate the cross-sectional configuration of the drive shaft 500. Preferably, the internal shoulders 370 avoids contact with the middle portion of the shaft 500 for precise alignment. In one embodiment, a stop 375 facilitates precise positioning of first collimating lens 340 and/or hollow drive shaft 500 within lens holder 350. The stop 375 prevents the lens 340 from moving proximally on the distal side of the stop 375 and the stop 375 prevents the motor shaft 500 from moving distally on the proximal side of the stop 375. In one embodiment, the stop 375 is integral with lens holder 350. Alternatively, the stop 375 could be fixedly attached to the distal end of lens holder 350.

The coupling 300 accommodates the rigid shaft 310, the first fiber ferrule 330, the first collimating lens 340, and the lens holder 350 in a way that transfers torque from the hollow drive shaft 500 to the rigid shaft 310, but also inhibits vibration of the rigid shaft 310 from affecting angular alignment of the first collimating lens 340. The accommodation of coupling 300 may be achieved by a configuration that provides for co-rotation or simultaneous rotation of the first optical fiber 320, the first fiber ferrule 330, and the first collimating lens 340 with the rigid shaft 310 without rigid or fixed attachment therebetween. The fit-up of shaft 500 and lens holder 350 is tightly controlled to provide more axial force and torque than is required to move the catheter core in its sheath and less axial force than would damage the bearings of motor 400. Shoulders 370 help control the spring constant and hence grip on the shaft. Elasticity and coefficient of thermal expansion of the lens holder 350 material are both carefully chosen to provide the required range of engagement force and torque over the require range of operating conditions, especially at rotational speeds as high as between about 10,000 and 20,000 RPM.

Figure 9C:
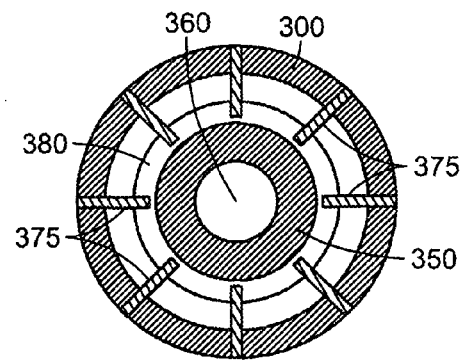
FIG. 9C is a cross-sectional view along the line 9C-9C of FIG. 9A.

For example, referring to FIGS. 9A-9C, in one embodiment, the lens holder 350 engages the coupling 300 by having at least a proximal end 355 including a cross-sectional shape that is not free to rotate within the distal end of a bore 365 of the coupling 300. Such a shape is illustrated in FIG. 9B as a square or rectangular cross-section; however, the cross-sectional shape of at least the proximal end 355 of the lens holder 350 and the distal end of the bore 365 may be any complementary shape that does not allow rotation of at least the proximal end 355 of the lens holder 350 within the bore 365, such as polygonal, triangular, pentagonal, hexagonal, octagonal, trapezoidal, and the like. Thus, the lens holder 350 is not fixedly held to the coupling 300; however, rotation of the lens holder 350 is coupled to rotation of the coupling 300, which, in turn is coupled to rotation of the rigid shaft 310.

The effects of vibration of the rigid shaft 310 may be reduced by decoupling transfer of moments between the lens holder 350 and the coupling 300 in a direction transverse to the longitudinal axis. Such decoupling may be achieved, for example, by a configuration including a plurality of pins 375 that are accommodated within one or more circumferential grooves 380 disposed in an outer surface of the lens holder 350, as illustrated in FIGS. 9A and 9C. The plurality of pins 375 may be spring loaded and biased inward, or may be press fit through corresponding holes (not shown) disposed radially through the coupling 300. Such a configuration including the plurality of pins 375 disposed in the one or more circumferential grooves 380 facilitates longitudinal application of force between the lens holder 350 and the coupling 300 without a fixed or rigid connection therebetween.

The design reduces the effect of vibration of rigid shaft 310 on the angular alignment of collimating lens 340. With respect to the 6 degrees of freedom between the fixed and rotating portions of the joint, roll or rotation is transmitted by the square end of the lens holder 350 engaging the square pocket in the coupling 300. Pitch and yaw, which are the transverse angular alignments to the roll/rotation, are left free. Longitudinal force, "Z", is transmitted by the pins 375 in groove 380. Transverse forces, "X" and "Y", are transmitted by the square end/square pocket apposition. In one embodiment, at least 2 pins 375 transmit a longitudinal force while allowing the pitch and yaw motion, as described above. This may be precisely symmetric with respect to pitch and yaw motions or asymmetric with respect to the pitch and yaw motions. Alternatively, the pins 375 could also provide transverse restraint.

The hollow drive shaft 500 is rotationally driven by the motor 400, as indicated by arrow 510 in FIG. 8A. In one embodiment, the motor 400 is disposed concentrically around the hollow drive shaft 500. Such an arrangement may facilitate a reduction in the number of moving parts and a reduction in size of the optical rotary joint 200. In other embodiments, the motor 400 may include a separate housing 450, as shown in FIG. 3A, and be disposed apart from the hollow drive shaft 500 such that the hollow drive shaft 500 is driven by the motor 400 via, for example, an external gear train, belt, chain, or other mechanism for transfer of torque from the motor 400 to the hollow drive shaft 500 as may be known in the art. An exemplary motor 400 capable of producing rotational speeds in excess of 10,000 RPM, alternatively between about 10,000 and 20,000, is available from Maxon Precision Motors, Inc. (Fall River, Mass.).

Figure 8B:
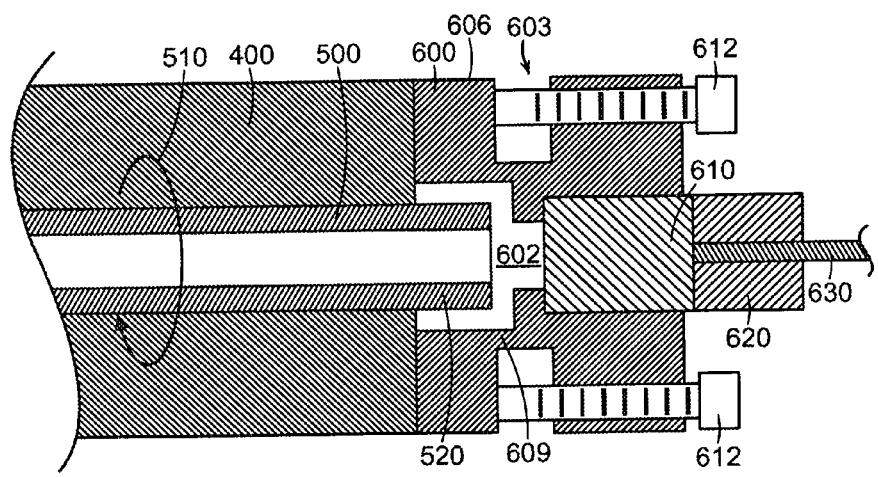
FIG. 8B illustrates a close-up view of section 8B of the proximal end of the optical rotary joint of FIG. 8A.
Figure 11:
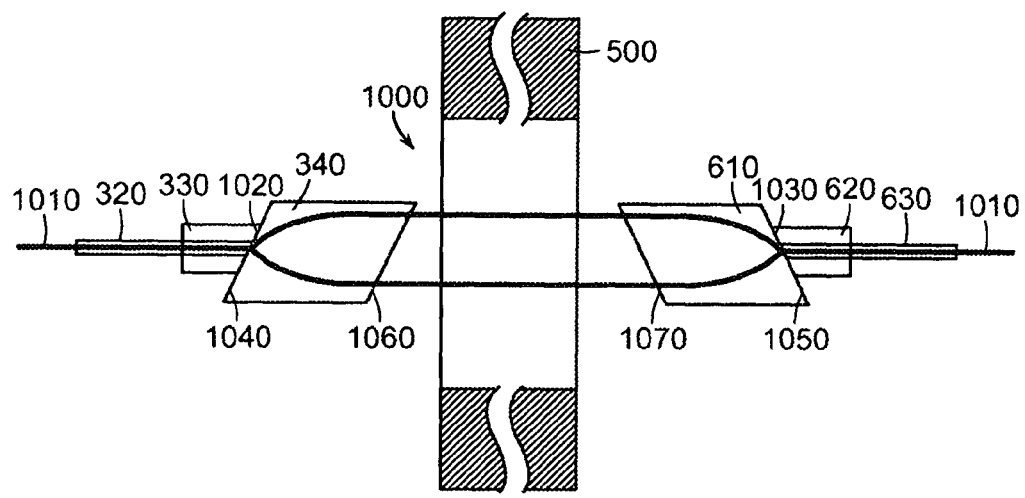
FIG. 11 illustrates an exemplary optical path through an optical rotary joint.

As shown in FIGS. 8A and 8B, a proximal end 520 of the hollow drive shaft 500 freely rotates proximate to a second collimating lens 610 fixedly held within the proximal end of the stationary lens holder 600. The stationary lens holder 600 includes a distal lumen 602 to receive the proximal end 520 of the hollow drive shaft 500 and freely rotate within the distal lumen 602. The second collimating lens 610 in the proximal end 610 is optically coupled to the optical path within the hollow drive shaft 500. The stationary lens holder 600 may be attached to the motor 400 via a connection method including by way of example and not limitation, a frictional fit, a snap fit, crimping, swaging, overmolding, an adhesive, a weld, a magnetic fit, and the like. A second fiber ferrule 620 is attached to a proximal end of the second collimating lens 610. The second fiber ferrule 620 fixedly connects over a distal end of a second optical fiber 630, as shown in FIG. 11, which delivers light to and/or receives light from the second collimating lens 610 from a light source (not shown), such that the light may pass from the second optical fiber 630 to the collimating lens 610. In one embodiment, the distal end of the second optical fiber 630 is coaxially disposed with the second fiber ferrule 620. The second optical fiber 630 may be a single mode or multi-mode optical fiber. The second fiber ferrule 620 is made from a material that has properties similar to that of the second optical fiber 630. For example, the second fiber ferrule 620 may be made from glass to match coefficient of thermal expansion with the second optical fiber 630. The second optical fiber 630 may be connected to the second fiber ferrule 620 by a connection method including by way of example and not limitation, an adhesive, a weld, splicing, fusion, etc. Alternatively, the second optical fiber 630 may be manufactured integrally with the second fiber ferrule 620.

As shown in FIG. 8B, the second collimating lens 610 is disposed in optical communication with a distal end of the second optical fiber 630. The second collimating lens 610 may be made from an optical material having an internally variable index of refraction and may be the same as or different from the first collimating lens 340 described hereinabove with regard to FIGS. 8A and 9A. For example, in one embodiment, the second collimating lens 610 is a lens having a radial index gradient such as a gradient index ("GRIN") or self-focusing ("SELFOC") lens. In other embodiments, other types of collimating lenses may be used, such as devices that narrows a beam of light or causes the directions of motion to become more aligned in a specific direction (i.e. collimated or parallel) or to cause the spatial cross section of the beam to become smaller.

In one embodiment, the second collimating lens 610 is fixedly attached to the distal end of the second fiber ferrule 620. The second collimating lens 610 may be attached to the second fiber ferrule 620 via a connection method including by way of example and not limitation, a frictional fit, a snap fit, an adhesive, etc. It is contemplated that the second fiber ferrule 620 facilitates stronger attachment of the second optical fiber 630 to the second collimating lens 610.

In another embodiment, the second collimating lens 610 is fixedly held by the stationary lens holder 600 by a connection method including by way of example and not limitation, a frictional fit, a snap fit, an adhesive, etc. The stationary lens holder 600 may be manufactured from a material including by way of example and not limitation, stainless steel, aluminum, or plastics such as polyetheretherketone (PEEK) or polyoxymethylene (POM).

As discussed above, the invention provides optical-electrical rotary joints and optical rotary joints for use with optical systems. A joint can have two lenses disposed therein for creating and aligning a light path through the joint. Further, in certain embodiments, joints of the invention include features to aid in the precise alignment of optical components.

For example, in some embodiments, stationary lens holder 600 includes deformable region 609 that is selectively deformed to align the second ferrule 620, the second fiber 630, and the second collimating lens 610 relative to the hollow drive shaft 500. As shown in FIG. 8B, an annular groove 603 can be provided that is disposed at an outer surface 606 of the stationary lens holder 600 resulting in a region 609 having reduced wall thickness. In this embodiment, alignment of the second ferrule 620, second fiber 630, and second collimating lens 610 is accomplished by deformation of the region 609 having reduced wall thickness. Deformation applied to the region 609 effectively adjusts the alignment of the second ferrule 620, second fiber 630, and second collimating lens 610 relative to the hollow drive shaft 500.

In one embodiment, a plurality of adjusters 612 may be provided disposed longitudinally through the stationary lens holder 600 and disposed across the annular groove 603, as illustrated in FIG. 8B. Suitable adjusters 612 may include, for example, screws, bolts, threaded rods, or other devices as known in the art. One or more of the adjusters 612 may be manipulated to deform the reduced diameter portion 603 of lens holder 600. The plurality of adjusters 612 may include any number of adjusters 612 as desired or appropriate to achieve the desired alignment.

In one embodiment the plurality of adjusters 612 may remain in place after alignment. Such arrangement may have the benefit of facilitating field adjustment of alignment if misalignment occurs. In another embodiment, the region 609 is permanently deformed to or near an optimal alignment and the plurality of adjusters 612 are removed. Such permanent deformation may be accomplished, for example, via application of heat during alignment via the plurality of adjusters 612 followed by removal of the heat to allow the region 609 to cool prior to removal of the plurality of adjusters 612.

In a further embodiment, an external device may be used to deform the region 609. For example, heat may be applied to the stationary lens holder 600 via a heated sleeve or other device (not shown) placed thereover. After heating the stationary lens holder 600 and manipulating the sleeve or other device (not shown) to selectively deform the region 609 as desired, the heat may be removed while leaving the sleeve or other device (not shown) in place to allow the region 609 to cool, thus permanently deforming the region 609 as desired. Other arrangements as known in the art may be applied to accomplish the desired deformation of the region 609.

In a further embodiment, combinations of alignment methods may be used, including for example and without limitation alignment and attachment of second fiber 630 and second ferrule 620 to second collimating lens 610 by means of UV-cured adhesive followed by alignment by means of deformation of lens holder 600 in region 609.

As discussed with reference to FIGS. 4A-7, optical-electrical rotary joints are provided that can be manually separated and re-coupled. An optical-electrical rotary joint allows optical communication and continuous electrical contact from an upstream side of a coupling to a downstream side of the coupling while the two sides of the coupling my rotate relative to one another. Further, as discussed with reference to FIGS. 8A-9B, the invention provides optical rotary joints that allow optical communication across a coupling while downstream components rotate relative to upstream components.

In a further aspect, the invention provides for optical and optical-electrical joints in which a downstream component (such as an imaging catheter in an OCT system) translates relative to an upstream component. In general, translation of a component refers to motion of the component in a direction that is substantially parallel to an axis of an optical path (e.g., optical path 711 in FIG. 4A) or substantially parallel to an axis of rotation in a rotary joint.

Figure 10A:
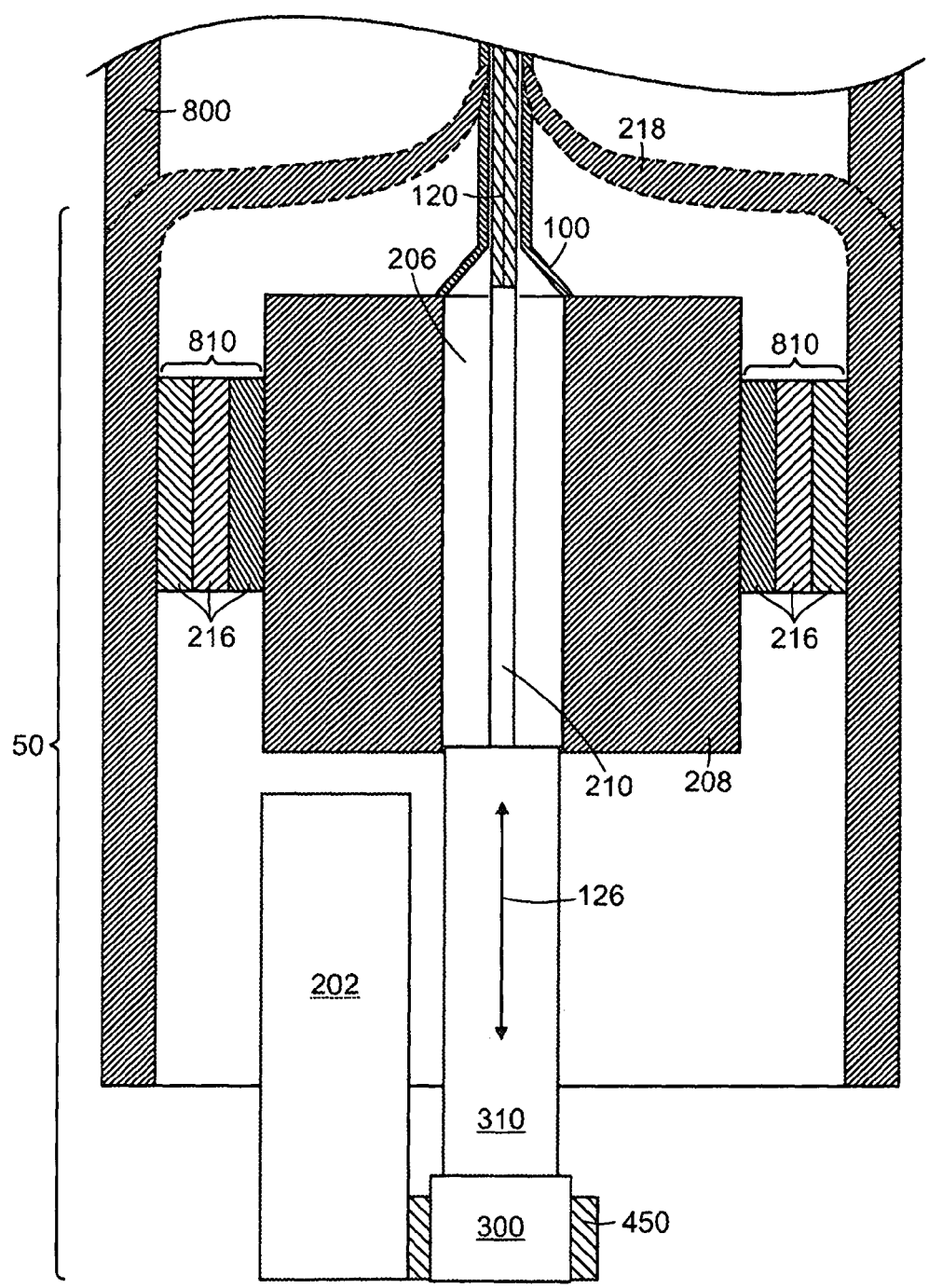
FIGS. 10A-10C illustrate a drive shaft assembly in three configurations.
Figure 10B:
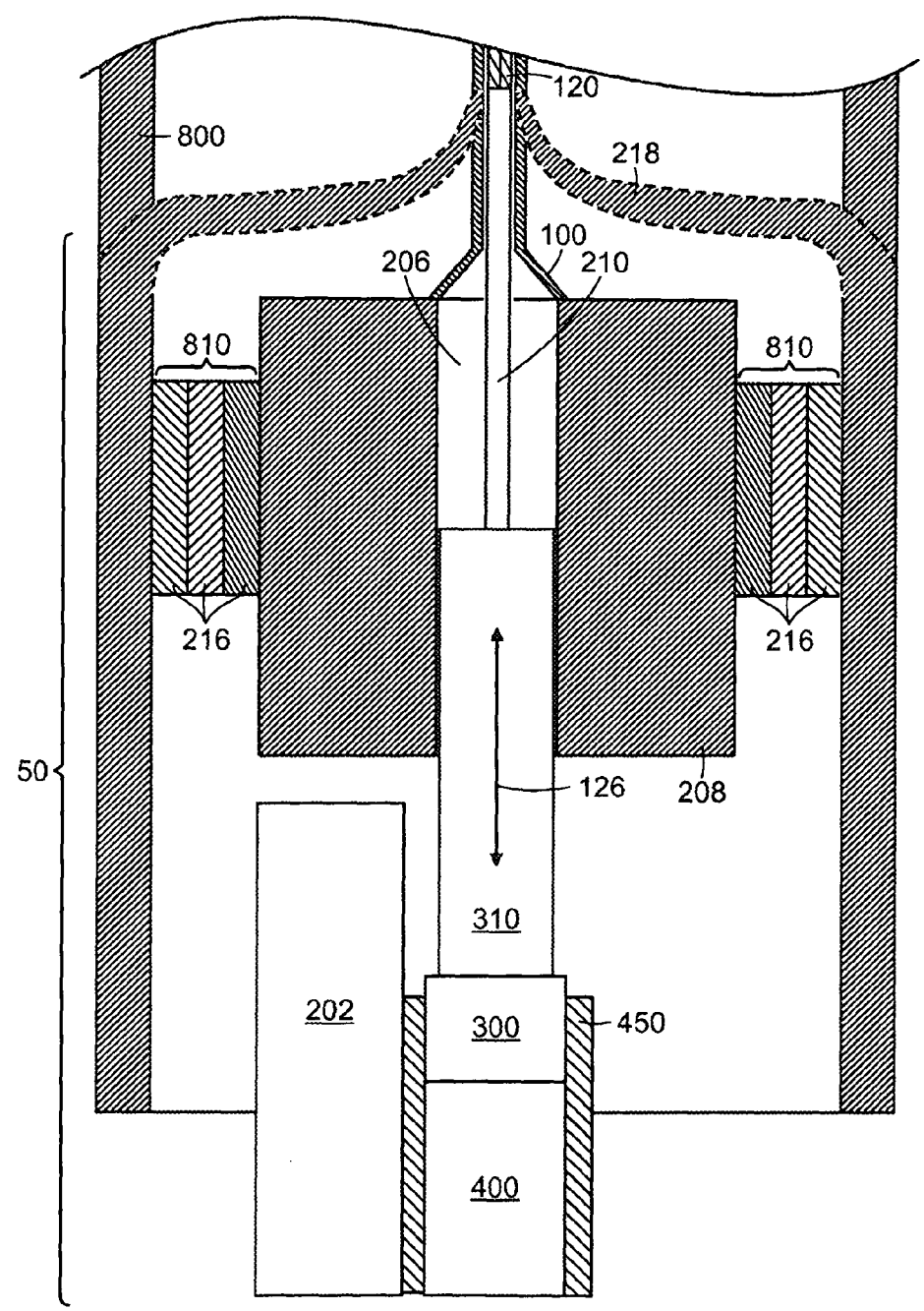
Figure 10C:
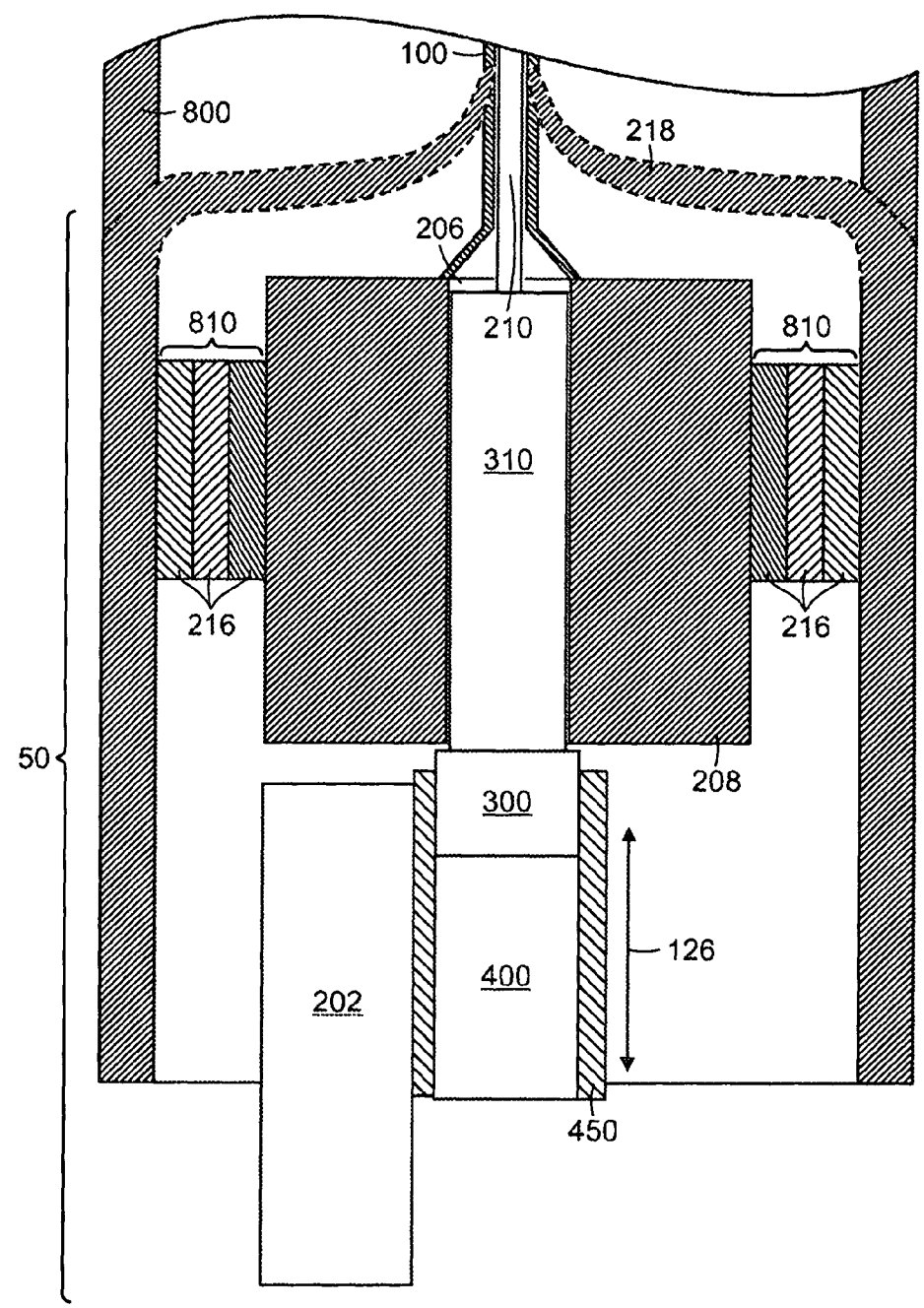

For example, FIG. 3A illustrates a support housing 208 disposed within catheter handle 800 as well as rigid shaft 310 and coupling 300. With coupling 300 coupled to motor 400, rigid shaft 310 can be translated relative to support housing 208. FIGS. 10A-10C illustrate a drive shaft assembly for translating rigid shaft 310 relative to support housing 208.

Referring to FIGS. 10A-10C, in one embodiment, portions of rotary joint 201, described above, may be utilized as part of a drive shaft assembly 50 that operationally connects the motor 400 to a flexible drive cable 120. The drive shaft assembly 50 may include the longitudinal translation mechanism or axially translatable drive stage 202 for longitudinal translation of the flexible drive cable 120 during rotation thereof. The axially translatable drive stage 202 may include a lead screw driven by a stepping motor or other mechanism for precise control of translation velocity and position of the motor 400. Thus, the flexible drive cable 120 may be translated longitudinally, as indicated by arrow 126 to provide a catheter "pull back".

As shown in FIGS. 10A-10C, in one embodiment, the drive shaft assembly 50 includes the stiffener or section of rigid shaft 310 that is sized to be self-supporting at the desired rotational speed and "pull-back" distance. A support housing 208 is coaxially disposed within the vibration dampening mechanism 810, and the support housing 208 includes a lumen 206, which is sized to accommodate at least a portion the rigid shaft 310. A distal end of the rigid shaft 310 is operably connected to a proximal end of a semi-rigid shaft 210. The semi-rigid shaft 210 is small enough to fit in the same lumen as a flex shaft 120 and flexible enough not to take a permanent set with some bending of the catheter sheath, but stiff enough to operate (transmit torque and axial force) within lumen 206 without failing. The semi-rigid shaft 210 may comprise nitinol, i.e. nickel titanium alloy, or another material such as stainless steel, tantalum, gold, platinum, titanium, copper, nickel, vanadium, zinc metal alloys thereof, copper-zinc-aluminum alloy, and combinations thereof. A proximal end of the flexible drive cable 120 is operably coupled to a distal end of the semi-rigid shaft 210.

Still referring to FIGS. 10A-10C, in one embodiment, the vibration dampening mechanism 810, for example, is an elastomeric vibration dampener 810, which may be disposed concentrically around the support housing 208 and between the support housing 208 and an external housing 800, for example, the catheter handle 800 disposed at a proximal end of a catheter sheath 100. The vibration dampening mechanism 810 may include one or more layers 216 of an elastomer or other mechanically compressible material and may thereby provide a mechanism to dampen high speed rotational vibrations on the proximal end of the drive shaft assembly 50. For example, the vibration dampening mechanism 810 may include a first layer, a second layer, and a third layer of an elastomer of varying degrees of compressibility to dampen the high speed rotational vibrations.

By dampening high speed rotational vibrations, the vibration dampening mechanism 810 inhibits catastrophic failure of the drive shaft assembly 50 when axially translated or "pulled back" by the translatable drive stage 202 during rotation at speeds in excess of 10,000 rpm, alternatively between about 5,000 and 25,000 rpm. Without the vibration dampening mechanism 810, the semi-rigid shaft 210 is limited in amplitude of vibration by the support housing 208; however, in the presence of the vibration dampening mechanism 810, the semi-rigid shaft 210 may additionally be inhibited from excessive vibration amplitude. Thus, the vibration dampening mechanism 810 facilitates a longer range of translation or "pull back" for a given configuration of the rigid shaft 310, the support housing 208, and the semi-rigid shaft 210. The vibrational dampening mechanism 810 may provide dampening further inhibiting the rotational vibrations from being translated to the distal end of the drive shaft assembly 50. Such dampening may also be beneficial for maintaining alignment of optics and therefore maintaining signal integrity along an optical path through the support housing 208.

Referring to FIGS. 10A-10C, operation of the drive shaft assembly 50 may begin, for example, in the configuration illustrated in FIG. 10C, wherein the stiffener or rigid shaft 310 is accommodated substantially coaxially within the lumen 206 of the support housing 208, which is fixedly attached to the external housing 800 via the vibration dampening mechanism 810. In this configuration, the semi-rigid shaft 210 is supported within the catheter sheath 100. In all of the configurations to be described below with regard to FIGS. 10A-10C, the flexible drive cable 120 is supported by the catheter sheath 100. In this configuration, the semi-rigid shaft 210 is supported within the catheter sheath 100.

In one embodiment, the catheter sheath 100 may include the external housing 800 disposed on a proximal end thereof, as illustrated by regions enclosed by dashed lines 218 in FIGS. 10A-10C. The flexible drive cable 120 and the semi-rigid shaft 210 are operably coupled with the distal end of the stiffener or rigid shaft 310. The stiffener or rigid shaft 310 is sufficiently rigid and/or has a sufficient diameter to be self-supporting in free space; however, in this configuration the rigid shaft 310 is further supported against large amplitude wobbling or flopping at rotational speeds in excess of 10,000 rpm (alternatively, between about 5,000 and 25,000 rpm) by an inner wall of the support housing 208. Such support of the flexible drive cable 120, the semi-rigid shaft 210, and the stiffener or rigid shaft 310 facilitates maintenance of a uniform rotational speed thereof.

FIG. 10B represents the drive shaft assembly 50 configured such that the flexible drive cable 120 and the semi-rigid shaft 210 are translated proximally relative to the configuration illustrated in FIG. 10C (or distally relative to the configuration illustrated in FIG. 10A). In this configuration, the flexible drive cable 120 remains supported within the catheter sheath 100 and operably coupled with the semi-rigid shaft 210 on the proximal end of the catheter sheath 100. The semi-rigid shaft 210 is supported on a distal end by the catheter sheath 100 and on a proximal end by connection to the stiffener or rigid shaft 310. In this configuration the semi-rigid shaft 210 is supported against large amplitude wobbling or flopping at rotational speeds in excess of 10,000 rpm (alternatively, between about 5,000 and 25,000 rpm) by an inner wall of the lumen 206 of the support housing 208. As noted with regard to FIG. 10C, the stiffener or rigid shaft 310 is sufficiently rigid and/or has a sufficient diameter to be self-supporting in free space. However, in this configuration the stiffener or rigid shaft 310 is further supported by being partially within the proximal end of the support housing 208, and is therefore further supported against large amplitude wobbling or flopping at rotational speeds in excess of 10,000 rpm (alternatively, between about 5,000 and 25,000 rpm) by the inner wall of the support housing 208. The proximal end of the stiffener or rigid shaft 310 extends from the proximal end of the lumen 206 and is operably coupled with the drive motor 400 via the coupling 300. Such support of the flexible drive cable 120, the semi-rigid shaft 210, and the stiffener or rigid shaft 310 facilitates maintenance of a uniform rotational speed thereof.

Referring once again to FIG. 10A, in this configuration the stiffener or rigid shaft 310 has been translated proximally relative to the configuration illustrated in FIG. 10B so as to be substantially external to the proximal end of the lumen 206 of the support housing 208. The semi-rigid shaft 210 is now disposed substantially within the support housing 208; however, the flexible drive cable 120 remains within the catheter sheath 100 and operably coupled to the metal semi-rigid shaft 210 at the distal end of the support housing 208. Thus, the flexible drive cable 120 remains supported within the catheter sheath 100. Accordingly, an optical rotary joint or an optical-electrical rotary joint may include a mechanism to provide translation of a downstream component relative to an upstream component.

Optical rotary joints (optionally with electrical rotary joint components) transmit light between an upstream portion and a downstream portion. Light may be transmitted by any method known in the art including, for example, conversion to an electrical signal for transmission over an electrical coupling or transmission through a solid medium such as glass or a gain medium. In certain embodiments, light is transmitted from an upstream component to a downstream component through free space (i.e., air, a gas, or a vacuum). In some embodiments, light is transmitted through free space coaxially with, and down the center of, hollow drive shaft 500 of motor 400.

Light transmission through the hollow drive shaft 500 is achieved without any optical components disposed therein. Referring to FIG. 11, an optical path 1000 may be represented as a beam of light 1010 traced through the optical rotary joint 200 between the first optical fiber 320 and the second optical fiber 630. A window at the distal tip in the hollow drive shaft 500 may be implemented for keeping out contamination.

Describing the optical path 1000 from left to right in FIG. 11, the first optical fiber 320 and the first collimating lens 340 are optically aligned to pass a signal longitudinally therebetween. First fiber ferrule 330 facilitates a mechanical connection between the first optical fiber 320 and the first collimating lens 340, but is not essential and may be absent or replaced by other elements in other embodiments. Similarly, the second collimating lens 610 and the second optical fiber 630 are optically aligned to pass a signal longitudinally therebetween. Second fiber ferrule 620 facilitates a mechanical connection between the second collimating lens 610 and the second optical fiber 630, but may be absent or replaced by other elements in other embodiments.

In one embodiment, this alignment is via physical connection, as described hereinabove with regard to FIGS. 1A and 2A. Other embodiments may include a physical gap between, for example, the first collimating lens 340 and the first optical fiber 320. The coupling 300, the rigid shaft 310, the first optical fiber 320, the first fiber ferrule 330, the first collimating lens 340, and the lens holder 350 rotate together as a unit driven by the hollow drive shaft 500.

Referring to FIG. 11, following the beam 1010 from left to right, the beam 1010 passes through the first optical fiber 320 into the first collimator lens 340. The beam 1010 is expanded and collimated by the first collimator lens 340 and freely passes through the hollow drive shaft 500. After passing through the hollow drive shaft 500, the beam 1010, collimated as a result of passing through the first collimator lens 340, enters the second collimator lens 610, which contracts the beam 1010 as illustrated. The contracted beam 1010 passes from the second collimator lens 610 into the second optical fiber 630. Alternatively, the light may pass from the second optical fiber 630 to the collimator lens 610.

In one embodiment, the first and second fibers 320, 630 and ferrules 330, 620 include angled surfaces 1020, 1030, respectively. Similarly, the first and second collimator lenses 340, 610 may include angled surfaces 1040, 1050, respectively, adjacently disposed to the angled surfaces 1020, 1030, respectively. The first and second collimator lenses 340, 610 may further include angled surfaces 1060, 1070, respectively, disposed opposite from the angled surfaces 1040, 1050, respectively. As known in the art, the angled surfaces 1020, 1030, 1040, 1050, 1060, and 1070 help to inhibit back reflection of the beam 1010.

Figure 12:
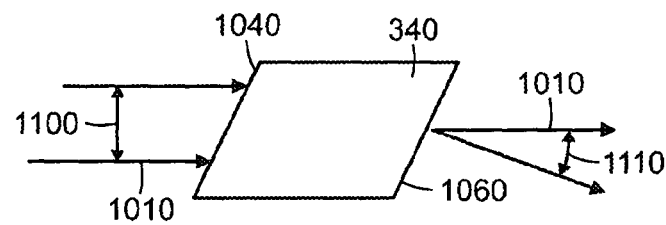
FIG. 12 illustrates the effect of angled lens surfaces on lateral offset of an input beam.
Figure 13:
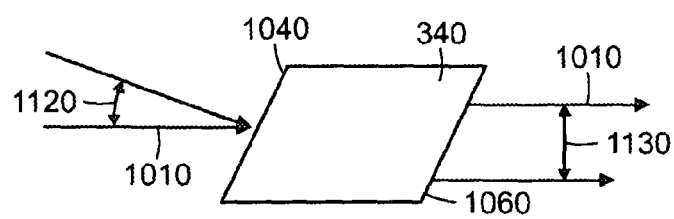
FIG. 13 shows the effect of angled lens surfaces on a change of angle of an input beam.

A light beam crossing an interface between material surfaces disposed at a non-orthogonal angle relative to the light beam and having dissimilar indices of refraction will be refracted. When utilizing a lens having a lens having a radial index gradient, an offset of a beam upon entry to the lens may result in an offset of the beam upon exit from the lens. For example, referring to FIG. 12, a lateral offset 1100 of the beam 1010 upon entry into a collimator lens, for example, the first collimator lens 340 having the angled surfaces 1040 and 1060, may result in a change in the output angle 1110 at which the beam 1010 exits the collimator lens 340. Similarly, referring to FIG. 13, a change of input angle 1120 of the beam 1010 upon entry into a collimator lens, for example, the first collimator lens 340 having the angled surfaces 1040 and 1060, may result in a change in the output lateral offset 1130 at which the beam 1010 exits the collimator lens 340. Therefore, it may be difficult to manufacture optical assemblies with adequate angular and radial alignment for good performance.

However, an alignment method may be used to compensate for such angular and radial offsets. For example, in one embodiment of such an alignment method, manufacturing errors of angular and lateral alignment between collimating lenses 340, 610 can be eliminated or reduced to acceptable levels by alignment of first and second fibers 320, 630 in ferrules 330, 620 with respect to their collimating lenses 340, 610, as described above. Referring to FIG. 11, in one embodiment, optically transparent adhesive is used to join first ferrule 330, first fiber 320, and first collimating lens 340, the alignment being carried out before the adhesive is cured with UV light. Similarly optically transparent adhesive may be used to join second ferrule 620, second fiber 630, and second collimating lens 610, the alignment being carried out before the adhesive is cured with UV light.

As discussed and shown herein, a mechanically simple, compact, optical-electrical rotary joint that reliably operates to transmit light and current between stationary and rotating components with low losses and excellent signal integrity at rotational speeds in excess of 10,000 RPM (alternatively, between about 5,000 and 25,000 rpm) is presented. The optical-electrical rotary joint includes a concentrically driven hollow drive shaft through which light is transmitted without any optical components disposed therein. Electrical contact mechanisms are provided to conduct current in one or more conductive lines across the joint. The light, the current, or both can carry a signal (i.e., encoded information). Further, mechanisms are presented that allow for translation of a downstream component of an optical-electrical rotary joint relative to an upstream component. The invention further provides optical rotary joints such as, for example, a fiber optic rotary joint or FORJ.

The simple design of the hollow drive shaft facilitates ease of replacement of a faulty motor in the field and reduces the cost and complexity of the optical rotary joint. The manually operable coupling mechanism and re-connectable optical and electrical connections disclosed herein allow for components on either side of a joint to be removed and replaced or treated separately. Thus, the invention allows for an optical-electrical system in which a component is replaceable or disposable while another component is persistent. In some embodiments, an OCT system is provided with a PIM coupled to an imaging engine to operate with a disposable or replaceable imaging catheter.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the optical rotary joint described herein and to teach the best mode of carrying out the same.

What is claimed is:

1. A method for carrying current and light across a rotating joint, the method comprising:
   transmitting light between an upstream instrument comprising a hollow drive shaft and a downstream component comprising a coupling and a rigid shaft in optical communication with the hollow drive shaft;
   conducting electricity from the instrument to the component; and rotating the component relative to the instrument while transmitting the light and conducting the electricity; and
   driving the rotation with a motor that remains stationary relative to the instrument;
   wherein the component comprises an optical line disposed coaxially with a drive shaft of the motor.

* * * * *